US009587213B2

(12) United States Patent
Morgan et al.

(10) Patent No.: US 9,587,213 B2
(45) Date of Patent: Mar. 7, 2017

(54) METHODS AND DEVICES FOR ENCAPSULATING CELLS

(71) Applicant: Brown University, Providence, RI (US)

(72) Inventors: Jeffrey Morgan, Providence, RI (US); Peter Chai, Providence, RI (US); Anthony Napolitano, Providence, RI (US); Edith Mathiowitz, Providence, RI (US); Dylan Dean, Providence, RI (US)

(73) Assignee: Brown University, Providence, RI (US)

( * ) Notice: Subject to any disclaimer, the term of this patent is extended or adjusted under 35 U.S.C. 154(b) by 985 days.

(21) Appl. No.: 13/749,267

(22) Filed: Jan. 24, 2013

(65) Prior Publication Data
US 2013/0137155 A1 May 30, 2013

Related U.S. Application Data

(62) Division of application No. 12/087,937, filed as application No. PCT/US2007/002050 on Jan. 24, 2007, now Pat. No. 8,361,781.

(60) Provisional application No. 60/796,771, filed on May 2, 2006, provisional application No. 60/761,800, filed on Jan. 24, 2006.

(51) Int. Cl.
*C12M 1/12* (2006.01)
*C12N 5/00* (2006.01)
*C12M 1/32* (2006.01)

(52) U.S. Cl.
CPC ............ *C12M 25/00* (2013.01); *C12M 23/12* (2013.01); *C12M 25/14* (2013.01); *C12N 5/0012* (2013.01); *C12N 5/0062* (2013.01); *C12N 2533/40* (2013.01); *C12N 2533/74* (2013.01)

(58) Field of Classification Search
CPC .................................................... C12M 25/14
See application file for complete search history.

(56) References Cited

U.S. PATENT DOCUMENTS

| | | | |
|---|---|---|---|
| 5,650,164 | A | 7/1997 | Della Valle et al. |
| 7,887,843 | B2 | 2/2011 | Libera et al. |
| 8,361,781 | B2 | 1/2013 | Morgan et al. |
| 8,501,476 | B2 | 8/2013 | Morgan et al. |
| 2003/0153078 | A1 | 8/2003 | Libera et al. |
| 2005/0169962 | A1 | 8/2005 | Bhatia et al. |
| 2011/0212481 | A1 | 9/2011 | Morgan et al. |
| 2013/0079288 | A1 | 3/2013 | Morgan et al. |
| 2013/0109625 | A1 | 5/2013 | Morgan et al. |

FOREIGN PATENT DOCUMENTS

| | | |
|---|---|---|
| DE | 4132379 A1 | 4/1993 |
| EP | 1 367 119 | 12/2003 |
| JP | 08-140673 | 6/1996 |
| JP | 2000-069957 | 3/2000 |
| JP | 2003-052361 | 2/2003 |
| JP | 2004-089136 | 3/2004 |
| JP | 2004-097047 | 4/2004 |
| JP | 2004-121168 | 4/2004 |
| JP | 2005160596 | 6/2005 |
| JP | 2006-055069 | 3/2006 |
| WO | WO 93/07258 | 4/1993 |
| WO | WO 95/31184 | 11/1995 |
| WO | WO 99/52356 | 10/1999 |
| WO | WO 03/059072 A1 | 7/2003 |
| WO | WO 2005/077013 | 8/2005 |

OTHER PUBLICATIONS

Supplementary European Search Report, dated Sep. 9, 2009, issued in EPO 7762405.4; titled "Cell Aggregation and Encapsulation Device and Method", 7 pages.
Dean, Dylan M., et al., "Rods, tori, and honeycombs: the directed self-assembly of microtissues with prescribed microscale geometries," *The FASEB Journal*, 21:4005-4012 (2007).
English Translation of JP 2006-055069, downloaded from http://www4.ipdl.inpit.go.jp on Nov. 2, 2011.
Folch, A. and Toner, M., "Microengineering of Cellular Interactions," *Annu. Rev. Biomed. Eng.*, 02:227-256 (2000).
Fukuda, J. and Nakazawa, K., "Orderly Arrangement of Hepatocyte Spheroids on a Microfabricated Chip," *Tissue Engineering*, 11(7/8):1254-1262 (2005).
International Preliminary Report on Patentability for International Application No. PCT/US2007/002050; titled "Cell Aggregation and Encapsulation Device and Method" date of issuance Nov. 27, 2008.
International Search Report, PCT/US07/02050; titled "Cell Aggregation and Encapsulation Device and Method", mailing date Oct. 9, 2008.
Jakab, K., et al., "Engineering biological structures of prescribed shape using self-assembling multicellular systems", *Proc. of the Nat. Academy of Sciences of the USA (PNAS)*, 101(9): 2864-2869 (Mar. 2, 2004).
Kelm, J., et al., "Tissue-Transplant Fusion and Vascularization of Myocardial Microtissues and Macrotissues Implanted into Chicken Embryos and Rats", *Tissue Engineering*, 12(9): 2541-2553 (2006).
Kelm, J.M., and Fussenegger, M., "Microscale tissue engineering using gravity-enforced cell assembly," *Trends in Biotechnology*, 22(4):197-202 (2004).
Mironov, V., et al., "Organ printing: computer-aided jet-based 3D tissue engineering", *Trends in Biotechnology*, 21(4): 157-161 (Apr. 2003).

(Continued)

*Primary Examiner* — Robert Yamasaki
*Assistant Examiner* — Teresa E Knight
(74) *Attorney, Agent, or Firm* — Hamilton, Brook, Smith & Reynolds, P.C.

(57) ABSTRACT

Molds for making cell aggregation devices include upper and lower surfaces. Methods of aggregating cells include depositing cells on in a seeding chamber, incubating the cells and removing aggregated cells. Devices for encapsulating aggregates of cells include biocompatible, bio-sustainable substrates compartments and a coating of a biocompatible, bio-sustainable polymer that completely surrounds the substrate and cell-encapsulating compartments.

7 Claims, 9 Drawing Sheets

(56) References Cited

OTHER PUBLICATIONS

Napolitano, A.P., et al., "Dynamics of the Self-Assembly of Complex Cellular Aggregates on Micromolded Nonadhesive Hydrogels," *Tissue Engineering*, 13(8):2087-2094 (2007).

Napolitano, A.P., et al., "Scaffold-free Three-Dimensional Cell Culture Utilizing Micromolded Nonadhesive Hydrogels," *BioTechniques*, 43:494-500 (2007).

Non-Final Office Action for U.S. Appl. No. 12/087,937 mailed Dec. 30, 2011.

Non-Final Office Action for U.S. Appl. No. 12/087,937 mailed May 12, 2011.

Notice of Allowance for U.S. Appl. No. 12/087,937 mailed Sep. 20, 2012.

Rago, A.P., et al., "Miniaturization of an Anoikis Assay Using Non-Adhesive Micromolded Hydrogels," *Cytotechnology*, 56:81-90 (2008).

Yeh, J., et al., "Micromolding of Shape-Controlled, Harvestable Cell-Laden Hydrogels," *Biomaterials*, 27:5391-5398 (2006).

Office Action, U.S. Appl. No. 12/087,937, "Cell Aggregation and Encapsulation Device and Method" mailing date Oct. 5, 2010.

METHODS AND DEVICES FOR ENCAPSULATING CELLS

RELATED APPLICATIONS

This application is a divisional of U.S. application Ser. No. 12/087,937, with a 371(c) date of Jul. 17, 2008, now U.S. Pat. No. 8,361,781, which is the U.S. National Stage of International application Ser. No. PCT/US2007/002050, filed on Jan. 24, 2007, published in English, which claims the benefit of U.S. Provisional Application No. 60/796,771, filed on May 2, 2006, and of U.S. Provisional Application No. 60/761,800, filed on Jan. 24, 2006. The entire teachings of the above applications are incorporated herein by reference.

FIELD OF THE INVENTION

The invention concerns cell culture aggregation and encapsulation devices and methods useful in cell culture and in tissue engineering and reconstruction techniques.

BACKGROUND OF THE INVENTION

The laboratory study of cells and groups of cells has been hampered by the inability to reproduce the cell's native environment on the benchtop. For example embryonic stem cells plated on microtiter plates do not aggregate into homogeneous embryoid bodies in a controlled and reproducible manner; they grow across the entire bottom surface of the plate. Unlike cells cultured on a monolayer, aggregated cells tend to retain their in vivo morphology, and as a result, produce more signaling factors. By their nature, because aggregates are formed through cell-cell junctions, the possibility of anoikis is greatly reduced, allowing aggregates to remain viable over significantly longer periods of time. Aggregates allow cells to be packed into close proximity with each other. Thus, the ratio of cells to volume in a microcapsule is larger. In addition, aggregated cells produce more signaling factors and target proteins so that scale-up is attainable.

Currently, two primary techniques are employed to make cells aggregate. In the hanging drop technique, the liquid cell cultivation medium containing the cells is applied to a slide, which is then inverted. Inversion causes the drop of cultivation medium containing the cells to sink downward but not make contact with a solid surface. Because the cells have no solid surface onto which to adhere, they aggregate and, in the case of stem cells, form embryoid bodies as if they existed in vivo and the surface tension of the drops prevents escape of the cells from the drops. See Kelm and Fussenegger, Microscale tissue engineering using gravity-enforced cell assembly, TRENDS in Biotechnology 22: 195-202 (2004) for a review and description of the technique. The disadvantage of the hanging drop technique is that scaling up the technique has been unsuccessful due to the difficulty of handling large numbers of drops in parallel (i.e. in an array) and the small volumes necessitated. Another disadvantage is that it is difficult to replenish or change the composition of the culture medium or add new cells to the aggregates in these hanging drops. Top-loading, in which a defined volume of liquid is applied to a base from above and then turned over causing the drop to hang, has improved the method somewhat but not solved the array issue so the technique is still highly labor intensive.

In the spinner culture technique, cells are placed in cultivation media and spun or actively mixed. The appropriate speed of mixing conducive to the formation of aggregates must be experimentally determined: if it is too fast, the cells may be damaged or the aggregates may become excessively large. Further, the size of the resulting cell aggregates is uncontrollable and variable, and results rarely reproducible. Moreover, cells are subjected to significant shear forces during the mixing process. Shear forces are known to influence cell behavior and cell responses. Also cells with relatively weak intercellular adhesion may not readily form aggregates in this high shear environment.

One additional known method, limited to cells that divide and then form aggregates, is cell culture in methyl cellulose or soft agar. A suspension of cells is resuspended in methyl cellulose or molten soft agar and the cells are trapped at various random x, y and z locations within the viscous methylcellulose or gelled soft agar. The cells are suspended within these matrices and are unable to interact with neighboring cells to form aggregates. Only those cells, particularly cancerous or precancerous cells that can proliferate, will form aggregates by virtue of the fact that as they proliferate they grow into aggregates of cells. Ordered arrays of aggregates cannot be made because the cells are randomly dispersed within the viscous gel-like methyl cellulose or the gelled soft agar. The method is not generally applicable to cell aggregation; it is in essence a cell suspension technique as aggregation will not result for a wide variety of cell types and is limited to those cells that actively proliferate under these particular circumstances.

More recent work in the field is evidenced by United States Patent Publication No. 2003/0224510, which discloses a method of forming aggregates of cells by the application of pressure or centrifugal force to cell suspensions on permeable membranes or in hollow fibers. Also, Fukuda et al., Orderly Arrangement of Hepatocyte Spheroids on a Microfabricated Chip, Tissue Engineering 11: 1254-62 (2005), discloses a method of preparing spherical multicellular hepatocyte aggregates in polystyrene chip cavities with the application of a turning force. And Fukuda et al., Novel hepatocyte culture system developed using microfabrication and collagen/polyethylene glycol microcontact printing, Biomaterials, in press, (2005), discloses a polymethylmethacrylate (PMMA) microarray with cylindrical cavities having bottoms with a defined collagen-modified region onto which hepatocytes adhered and formed spheroids. The other regions of the cavities were modified with polyethylene glycol to create regions of non-adherence.

Hydrogels are colloids composed of a three-dimensional network of hydrophilic polymer chains crosslinked via chemical or physical bonding. The polymers are in the external or dispersion phase and water, present in at least 10% of the total weight (or volume), is in the internal or dispersed phase (superabsorbent hydrogels have water contents exceeding 95%). Upon cross-linking the polymer chains form a solid, three-dimensional, open-lattice type structure that can hold water or other liquids.

Hydrogels have found utility in a variety of applications: in contact lenses, as wound dressings, as medical devices such as venous catheters, as cartilage implants and in drug delivery. Hydrogels have been used widely in the development of biocompatible biomaterials, due to their low interfacial tension and low frictional surface by the presence of water on the surface. Tissue engineers use them as scaffolds for cell growth and differentiation. There are many types of hydrogels and most are suitable for some purposes and not suitable for other purposes. Hydrogels can be composed of alginate, gelatin, chitosan, pluronic, collagen, agarose, polysaccharides, proteins, polyphosphazenes, polyoxyethylene-polyoxypropylene block polymers, polyoxyethylene-polyoxypropylene block polymers of ethylene diamine, polyacrylic acids, polymethacrylic acids, copolymers of acrylic acid and methacrylic acid, polyvinyl acetates and alcohols and sulfonated polymers. Some are pH and temperature sensitive. (See Park et al., Synthesis and characterization of pH- and/or temperature-sensitive hydrogels, *J. Applied Polymer Sci.* 46: 659-71 (2003).) Others are light-sensitive, pressure-responsive, electro-sensitive or responsive to specific molecules. (See, Park et al., Environment-sensitive hydrogels for drug delivery, *Advanced Drug Delivery Reviews* 53: 321-39 (2001).) To our knowledge, employing hydrogels for cell aggregation has not been investigated, although United States Patent Publication No. 2005/0196452 to Boyan et al. discloses the use of hydrogels, especially polyvinyl alcohol hydrogels, as implants for tissue repair. The hydrogels of Boyan et al are surface-modified with a textured surface composed of pores or recesses having defined characteristics to promote attachment and acceptance of the implant and to provide physical stimulation of cells to enhance osteoblast differentiation and proliferation. It is stated that the size of the pores comprising the textured surface of the hydrogel can aid in promoting adhesion of one cell type over another.

DESCRIPTION OF THE INVENTION

Surprisingly, we have found that molded hydrogels cause the aggregation of cells of a variety of cell types, in the absence of any forces or regional modifications to force the cells together or to cause the cells to adhere to each other. The cells aggregate without adherence to the hydrogel substrate. This controlled cell aggregation requires a surface shaped to funnel cells together that is at least partially cell-repellant. The combination of surface properties and geometry acts to increase the intercellular interaction and cell-to-cell adhesion. In contrast to the disclosure of Boyan et al., supra, which fails to teach anything about whether gravity pays a role in the structure or function of the device, and relies on a textured surface to assist in cell adhesion and enable implantation, the cell aggregation device of our invention is gravity dependent. We have also found that cells aggregate with predictable characteristics and dynamics that are dependent upon cell-type. However, these programmed aggregation characteristics and dynamics can be modified by modifying the shape of the aggregation structure employed in the aggregation process and/or by the addition of aggregation modification agents. Advantageously, cells aggregated in the device of the invention may then be readily encapsulated using the same device employed for aggregation, either with or without the addition of aggregation modification agents. Armed with the knowledge of the programmed aggregation characteristics and dynamics of the cells and with the means of modifying those characteristics and dynamics the skilled artisan in the field of tissue culture and engineering, by virtue of the teachings herein, is better able to control the aggregation process and attain scale-up, leading to structures, configurations and forms that may be employed in cell and tissue transplantation and reconstruction.

In one embodiment, the invention is a cell aggregation device comprising a hydrogel substrate having at least one, preferably a plurality, of cell-repellant compartments recessed into the uppermost surface. Each compartment is composed of an upper cell suspension seeding chamber having an open uppermost portion and a bottom portion, and one, or more than one, lower cell aggregation recess connected at the top to the bottom of the upper cell suspension seeding chamber by a port. The diameter of the port may be fully contiguous with the walls of the chambers and walls of the recesses, or the diameter of the port may be more narrow than the walls of the chamber but fully contiguous with the walls of the recesses or more narrow than both the walls of the chamber and the walls of the recesses.

The upper cell suspension seeding chambers are formed and positioned to funnel the cells into the lower cell aggregation recesses through gravitational force. The aggregation recesses are formed and positioned to promote cellular aggregation by coalescing cells into a finite region of minimum gravitational energy, increasing intercellular contact and minimizing or preventing cell adherence to the substrate.

All or a portion of each compartment may be recessed into the hydrogel or be bound by substantially vertical, i.e., upright walls that surround the hydrogel and extend upward from the top surface of the hydrogel. In either configuration, the cell suspension seeding chamber is defined by substantially upright walls or by tapered walls sloping inwardly from top to bottom, a substantially open mouth at the uppermost edge of the walls and a port or passage at the distal or lower edge of the walls connecting to the aggregation recess or recesses. Because cells settle quickly by gravitational forces once added to the upper cell suspension seeding chamber, the walls of the upper cell suspension seeding chamber do not necessarily need to be composed of a cell-repellant hydrogel, other materials, even those that normally would be cell adhesive in a horizontal position, may be used for the side walls of the cell seeding chamber. The aggregation recess or recesses are formed and positioned with walls depending from the walls of the cell suspension seeding chamber. The walls of the seeding chamber may be continuous in the vertical plane with the walls of the aggregation recesses or they may be discontinuous in the vertical plane with the aggregation recess walls such that a shoulder or dog is formed there between.

The aggregation recesses are further formed to contain a region of minimum gravitational energy depending from the walls of the aggregation recesses, i.e., the walls of the aggregation recesses terminate in a region of minimum gravitational energy. This region may be a small, flat surface having a width at the shortest axis of no more than about 2000 microns. More preferably this region may be a concave surface, a tapered surface terminating in a point, or a wedge-shaped tapered surface. The slope of a tapered surface of an aggregation recess may be an angle up to about 75 degrees off the vertical axis. The aggregation recesses may also comprise a combination of vertical and tapered or curved sections. For example an aggregation recess may have a vertically cylindrical upper region that is continuous with a hemispherical lower region forming a test tube-like recess or it may have an inwardly sloping upper region that is continuous with a hemispherical lower region forming a substantially parabolic recess.

The seeding chambers and the aggregation recesses may be formed in a variety of shapes. In plan view, the shape of each may be a circle, oval, torus, channel or any complex shape or combination of shapes. The shape of each chamber or recess may be the same or different. The seeding chamber is definable as a region constrained on all sides with walls, having an open top portion and a bottom surface. In the bottom surface are disposed and arranged the aggregation recesses, extending vertically toward the bottom of the device. The device is formed to permit a cell suspension to be poured into the seeding chamber and to enter the aggregation recesses by gravity flow. Gravity causes the cells in the suspension to be funneled from the seeding chamber into the uppermost portions of the aggregations recesses and to sink to the bottom of the recesses. Because the device will typically and preferably contain a plurality of aggregation recesses, the seeding chamber should be large enough to be able to hold a sufficient volume of cells in suspension to ensure that the cell suspension enters as many of the aggregation recesses as possible. Consequently, the greater the number of aggregation recesses, the larger the volume the cell suspension seeding chamber must be. Although one aggregation recess per seeding chamber is sufficient, for economy of scale purposes more than one aggregation recess per seeding chamber is preferable. The number of aggregation recesses per each seeding chamber will depend at least in part on the molding characteristics and abilities of the particular hydrogel chosen to make the device. Stiffer more rigid hydrogels will be able to maintain the shape of the aggregation recesses more readily than softer more malleable hydrogels and consequently cell aggregation devices made from these will be able to contain a greater number of aggregation recesses. The arrangement of the cell aggregation recesses within each of the seeding chambers is unimportant so long as the recesses are separated from each other by a sufficient distance such that the hydrogel material interposed between the recesses maintains its rigidity and does not collapse. One highly preferred parameter is transparency of the hydrogel. Transparent hydrogels are preferred materials because aggregation can readily be seen and the process readily monitored.

Another possibility is a hydrogel that is conditionally cell repellent. For example poly(N-isopropylacrylamide (PIPAAm) that can be polymerized into a hydrogel is a temperature responsive polymer that changes from hydrophilic (cell repellent) (e.g., 20° C.) to hydrophobic (cell adhesive) (e.g., 32° C.) as the temperature is increased. Thus at low temperature, cell aggregates could be formed in a hydrogel mold containing PIPAAm. Once the aggregates were formed, the temperature could be raised and the aggregates would be able to interact with themselves and the walls of the hydrogel.

The overall depth, width and length of the device may also vary depending upon the type of cell type, aggregate size, and hydrogel selected; the hydrogel chosen must be cell-repellant and moldable into a stable, structurally controllable form. For polyacrylamide hydrogels, we have found that a depth of at least 500 microns is desirable for both the seeding chamber and aggregation recesses resulting in an overall depth of at least 1000 microns. By "cell-repellant" we mean that upon curing, the hydrogel lacks the ability to adhere, affix, attach or stick to cells.

The device may be constructed with one or more than one media exchange ports. Media exchange ports are depressions or cut-outs in the outer vertical walls of the device that provide room to place a pipet tip between the device and the wall of the plate or Petri dish in which the device is incubated. The ports may be any shape so long as they are formed and positioned so as to permit the placement of a pipet tip between the device outer wall and the plate or, dish in which it sits. An arcuate shape is exemplary. This allows for fluid to be exchanged during experiments without disrupting the cells that are aggregating within the aggregations recesses of "the device.

Generally, the width of the cell seeding chambers of the device of the invention will be at least 2 mm from wall to opposing wall, measured by the shortest dimensional length for a rectangular or ovoid cross-sectional shape, or at least 2 mm in diameter for a circular or square cross-sectional shape. The depth of the cell seeding chambers should be at least 500 µm, preferably from about 1000 to about 2000 µm. The maximum depth should be about 5 cm.

The dimensions of the cell aggregation recesses may also vary depending upon the characteristics of the hydrogel. For polyacrylamide hydrogels the horizontal cross-sectional shortest length should be between 20 and 5000 µm, preferably between about 200 and 600 µm and the depth of the cell aggregation recesses should be at least 500 µm, preferably from about 500 to about 1000 µm. The maximum depth of the recesses is dictated by the thickness and elasticity of the polyacrylamide hydrogel substrate. The recesses may be fully disposed within the hydrogel substrate or the recesses may protrude from the bottom surface of the substrate.

The invention is exemplified using a polyacrylamide hydrogel, which is a preferred material due to its optical qualities, its lack of detectable interaction with cell surfaces, its known biocompatibility and the ability to control its flexibility by modifying the relative concentrations of acrylamide and bisacrylamide. The polyacrylamide hydrogel formed by polymerization of a mixture of acrylamide and the crosslinker bis acrylamide may have a polymer: crosslinker ratio of 5:1 to 100:1, more preferably a polymer: crosslinker ratio of 19:1 to 29:1 (w/w). However other polymeric materials, including other hydrogels, may be employed to create the devices of the invention. Such polymeric materials must be biocompatible, i.e., capable of existing with a biological compound and or cell without an adverse effect (e.g. toxicity) on the compound or cell. The materials chosen must also be "cell-repellant", i.e., incapable of adhering, attaching, affixing or sticking to the cells. The biocompatible polymeric materials may be naturally cell-repellant or may be modified to be cell repellant, for example by coating with or attachment or immobilization to polyethylene glycol (PEG). The biocompatible polymeric materials may be conditionally cell repellant polymers utilized in their cell repellant state. An example of a conditionally cell repellant polymer is N-isopropyl polyacrylamide (NIPAA), which is cell adhesive above 32° C. and cell repellant below 20° C. Alternatively, cell-type-dependant cell repellent polymeric materials may be employed for aggregation of cells known to be repelled by the material. For example Type I Collagen is a polymeric material known to be macrophage repellant. Consequently, it may be used as the polymeric material in a macrophage cell aggregation device of the invention, but it is adhesive to other cells such as fibroblasts and would therefore be inappropriate as the polymeric material in, for example, a fibroblast cell aggregation device.

The polymeric material must be moldable into a stable, structurally controllable form. Polymeric hydrogel materials for use in the devices of the invention may be formed by chemical cross-linking, by photo-polymerization, by ionic cross-linking, by hydrophobic cross-linking, by hydrogen bonding and any combination thereof. Methods of forming hydrogels are well known in the art. Exemplary ionically cross-linked hydro gels which may be employed include calcium alginate, and barium alginate. Exemplary hydrogels formed by hydrogen bonding include agar and agarose, the latter of which is preferred and is also exemplified herein. Exemplary hydrogels formed by chemical cross-linking include poly(ethylene glycol) (PEG), polyvinyl alcohol hydrogels (PV A), 2-hydroxyethyl methylacrylate (HEMA), copolymer of methyl methacrylate and 3-(t-butoxycarbonyl)-N-vinyl-2-pyrrolidone (MMA:TBNVP), hyaluronic acid (HA), poly(ethylene glycol)diacrylate (PEG-DA), poly (ethyl methacrylate) and tetrahydrofurfuryl methacrylate (PEMA/THFMA), sulfonated PEG. The hydrogel should have the ability to swell from 1% to 500% W/W.

In another embodiment the polymeric material may be composed of an interpenetrating polymer network (IPN). An IPN is a combination of two or more cross-linked polymers that are synthesized in juxtaposition and exhibit improved strength and mechanical properties compared with the individual components alone. An IPN of acrylamide, polyethylene glycol, and acrylic acid is an exemplary polymeric material that may be employed in the device of the invention.

The mold used to make the cell aggregation device of the invention can be made using known fabrication techniques. Free-form fabrication techniques can be employed to selectively control the shape of the structure and create microstructures using computer-aided design (CAD) followed by MEMS microfabrication or three-dimensional printing. The microfabrication process may use commercially available, epoxy-based photoresist and standard photolithography techniques know in the art to produce the specified surface architecture. Alternatively stereolithographic techniques, selective laser sintering, fused deposition processes, three-dimensional printing or OBJ processes may be employed. In sum, any method may be employed to manufacture the mold used to make the cell aggregation device. A preferred method to manufacture the mold used to make the cell aggregation device will have resolution capabilities in the x, y and z dimensions that enable it to fabricate this device. If a mold is employed to construct the cell aggregation device of the invention, the mold should be a negative replicate of the device, i.e., a negative replica or the negative three-dimensional image of an exact copy of the device such that upon casting, the device in the desired shape and having the desired dimensions results.

In addition to making a mold to be used to make the cell aggregation device, other methods may be applicable to the making of a cell aggregation device. Rather than a molding process, the hydrogel based cell aggregation device could be manufactured by a stamping method to create the recesses, or a laser ablation process to create the recesses or a particle leaching process to make the recesses.

In another embodiment the invention includes a method of aggregating cells comprising the steps of depositing a plurality of cells into an upper cell seeding chamber of a cell aggregation device of the invention, incubating said cells for time sufficient to allow the cells to aggregate, and removing the aggregated cells from the device. Optionally, the method may further comprise the step of adding one or more selected aggregation modifying agents to the cells. Preferably, the selected aggregation modifying agent(s) may be added to the cells prior to the incubation step. The addition of the aggregation modifying agent(s) affords precise control of the kinetics of and morphologies associated with cellular aggregation, which is fundamental for tissue engineering applications. Modification of aggregation with pharmacological intervention is efficient and allows for this control. As mentioned prior, not all cell types will self-assemble into complex shapes. By inhibiting such processes as cellular contraction and cytoskeletal activity (with such inhibitors as 2,3-butanedione monoxime, ML-7, Y-27632, cytochalasin D, colchicine, okadaic acid and mycalolide B, for example) cell adhesion (with antibodies such as anti-E-cadherin, anti-zo-1, or anti-connexin 32, for example), cell motility (via treatment with the motility inhibitor locostatin), or by stimulating cellular contraction (with lysophosphatidic acid, for example) complex shapes can be maintained during self-assembly.

In homotypic cellular aggregation, this means that complex shapes can be obtained by cell types that would normally progress to spheroids (such as fibroblasts treated with Y-27632 in honeycomb-shaped recesses as disclosed in the Examples). It also means that matrix production, cellular metabolism and other specialized cellular functions can be controlled both in level and timing of activity. In heterotypic aggregation, modification of such cellular behavior would result in control of sorting and final cellular position within spherical or complex-shaped aggregates. This would be crucial for tissue engineering applications, as any sorted positions of mixed cell types could be obtained by pre-treated one or multiple cell types before combining for aggregation. Therefore, final cell type position within heterotypic aggregates would not be subject only to differential adhesivities between cell types. Applying this principle in a blood brain barrier aggregate model, endothelial cells, which normally sort to the center with RG2 cells (a glioblastoma brain cancer cell line), could be pre-treated with an inhibitor of one of the aforementioned processes to get them to coat the RG2s. This would result in a microenvironment similar to the blood-brain barrier (BBB) and a large array of these aggregates could be used to test the efficiency of a drug designed to cross the BBB and treat glioblastomas.

For both homo- and heterotypic aggregates, "pausing" of cellular assembly at different stages via pharmacological intervention opens several possibilities for tissue engineering. For example, if a complex-shaped aggregate could be "paused" before surface cells had altered their morphologies and lost visible intercellular boundaries, it is possible that with the addition of an endothelial cell type at this point, the aggregate would allow for more efficient "prevascularization"—a key challenge in organ transplant technology.

Because any aggregation modifying agent may be employed in the invention, it is likely that any complex shape can be achieved with any cell type. As organs in the body have different intrinsic architectures, this means that any structure and combination of structures can be designed in vitro to be tailored for more efficient transplantation or grafting. Further, more in vivo-like microtissues can be used in vitro for screening of therapeutic drugs. Control of cell sorting and motility with aggregation-modifying agents in vitro could also represent a model for studying various embryological disorders related to sorting and migration such as spina bifid a and cleft palates.

The aggregated cells may be used in research, in tissue engineering applications such as cell transplantation, in stem cell differentiation and in functional micro-tissue formation. The aggregated cells may be used for the production of therapeutic proteins, viruses for vaccines and other cell based products. The aggregates may be used for the screening of drugs. The device may be employed to retrieve products, for example secretory proteins, to introduce biochemical stimuli and to create three-dimensional biochemical gradients.

Virtually any type of cells may be aggregated using the device and method of the invention; there are no particular limitations with regard to the cells that may be employed, as long as the cells have the ability to aggregate (some cells, such as mature red blood cells and fully mature spermatozoa are not known to be able to aggregate). The cells may be prokaryotic or eukaryotic. Any type of mammalian cells, for example mice, rat, primate (especially human primate), chicken, porcine, bovine, equine cells, may be used. Either primary cultured cells or an established cell line can be employed. The primary cultured cells may originate from any tissue, e.g. cartilage, bone, skin, nerve, oral alimentary canal, liver, pancreas, kidney, gland, heart, muscle, tendon, fat, connective, reproductive organ tissue, ocular, blood vessel, bone marrow and blood. Exemplary cell types include osteoblasts, keratinocytes, melanocytes, hepatocytes, gliacytes, pancreatic beta cells, pancreatic exocrine cells, neural stem cells, neural precursor cells, spinal cord precursor cells, nerve cells, mammary gland cells, salivary gland cells, renal glomerular endothelial cells, tubular epithelial cells, adrenocortical and adrenomedullary cells, cardiomyocytes, chondrocytes, skeletal and smooth muscle cells, fat and fat precursor cells, corneal and crystalline lens cells, embryonic retina cells, vascular cells, endothelial cells, bone marrow stromal cells and lymphocytes. For example, the device and method of the invention may be employed to aggregate muscle cells (smooth, skeletal, cardiac), connective tissue cells (fibroblasts, monocytes, mast cells, granulocytes, plasma cells, osteoclasts, osteoblasts, osteocytes, chondrocytes), epithelial cells (from skin, gastrointestinal, urinary tract or reproductive tract, or organ epithelial cells from the liver, pancreas or spleen), or nervous system cells (glial, neuronal, astrocytes).

Additionally, aggregates of mammalian stem cells (embryonic, nonembryonic and hematopoietic) may be produced using the device and method of the invention. Upon aggregation, the stem cells form an "embryoid body". After a few days the aggregate forms a cystic embryoid body (essentially a hollow ball) and internal structures, for example a yolk sac or cardiomyocytes. The stem cell aggregates may be from differentiated stem cells, i.e. those with a distinct cell lineage prior to aggregation, or the stem cells may undergo differentiation in the cell aggregate after or during aggregation. Differentiation results in cells that have specific functions. Undifferentiated cells are pluripotent, i.e. they have not yet developed their specific function. Exemplary are stem cells of all types: ectodermal, mesodermal, endodermal, mesenchymal, hematopoietic, neural, hepatic, muscle, pancreatic, cutaneous, retinal and follicular stem cells.

Non-mammalian cells from any non-mammalian organism may also be used in the device. Numerous plant cell lines, animal cell lines, insect cell lines, plant virus cell lines and cells lines of microorganisms (such as Archaea, bacteria, plasmids, phages, yeasts and fungi exist) and are available from repositories known to those of skill in the art. (DSMZ, the German National Resource Centre for Biological Material is one; ATCC, the American Type Culture Collection is another.) Cells from any of the known repositories may be advantageously aggregated using the device and method of the invention.

The cells to be aggregated using the device and method of the invention may be native cells or genetically modified cells or mixtures thereof. Genetic modification to alter cellular RNA or DNA by addition, deletion or substitution is a well known technique in the art. One type of cells may be used or a combination of cell types may be used. Normal cells or abnormal cells may be aggregated in the device of the invention. Mixtures of normal and abnormal cells may be employed. Neoplastic or cancerous cells may be employed, such as for example, MC3T3-E1 cells that differentiate into osteoblasts and MC3T3-G2/PA6 cells that differentiate into fat cells. Any of the eleven SUM breast cancer cell lines that are well characterized and represent different subtypes of breast cancer including 44PE, 52PE, 102PT, 149PT, 11315MO2, 159PT, 185PE, 190PT, 225CWN, 229PE and other breast cancer cell lines including MDA-MB-435S, MDA-MB-231, MCF7, SK-OV-3, BJMC3879, MCF-7, MDAMB361, MFM223, BT549, MDAMB468, T-47D, BT474, SK-BR-3, HS578T can be used. Any of the prostate tumor cell lines including OPCT-1, OPCT-2, OPCT-3, DU145, LNCaP and PC-3 can be used. Any of the lung cancer cell lines including A549, NCI-H460, NCI-H1299 can be used. Any of the colon cancer cell lines including HCT116, HCT116p21−/−, HCT116p53−/−, HCT-15, HT-29, CaCo-2, CoLo205, SW48 can be used. Any of the skin cancer cell lines, including for example SK-MEL-28, SK-MEL-5, SK-N-SH, HT1080, P815, SW872, UMSCC-14A, KS SA1N, UACC903 and A-431, can be employed. Any of the brain cancer cell lines, including for example IMR-32, U-87 MG, A172, N1E115, SHSY5Y, A20, Neuro2A (N2a), SKNSH, C6, PC12, and U87, can be used. Any of the kidney cancer cell lines, including for example 786-O and ACHN, can be used. Any of the liver cancer cell lines, including for example HepG2, COLO 587, FaO, HTC and HuH7, can be used. Any of the bone cancer cell lines, including for example U-2 OS, can be used. Any of the ovarian cancer cell lines, including for example A2780, DOV13, OVCAR3, CoLo357 and HeLa, can be used. Any of the pancrease cancer cell lines, including for example Capan1, Panc1 and Panc89, can be used. Any of the adrenal cancer cell lines, including for example H295R and SW13, can be used. Any of the bladder cancer cell lines, including for example ECV304, can be used. Any of the bone/cartilage cell lines, including for example SAOS2, SW1353 and U2OS, can be used.

After aggregation, differentiation-inducing factors may be added to the cells. Such factors are known in the art; exemplary factors include for example stem cell growth factors, interleukins, interferons, tumor necrosis factors, colony stimulating factors, erythropoietin and thrombopoietin, insulin, indomethacin, dexamethasone and transferrin. Other agents, peptides, drugs or molecules can be added to promote or guide differentiation down certain pathways such as inhibitors of kinases, agonists or antagonists of receptors or interfering RNA or antisense oligonucleotides. The differentiated cells may then be employed in therapeutic methods. Alternatively, after aggregation of undifferentiated cells, the aggregates may be induced to differentiate upon transplantation into an animal.

The obtained aggregates may be employed alone, in combination with known tissue transplantation scaffolds, or in an encapsulated form as will be described later. In any form, they may be used to replace or augment damaged tissues and organs. For example, islet-like aggregates made using the device of the invention may be employed in the treatment of diabetes, dermal papilla cell aggregates may be employed to treat baldness, hepatocytes aggregates may be employed in the treatment of liver disease, dermal cell aggregates may be employed in cosmetic and reconstructive treatments of the skin and chondrocytes or osteoblasts aggregates may be employed in articular cartilage repair.

Aggregates of cancer or precancerous cells may be transplanted into laboratory animals to study tumor growth, metastasis, and treatment. Aggregates may also be used in the areas of high throughput drug screening and personalized medicine to measure drug efficacy or toxicity. Aggregates may be used to investigate or direct the differentiation of stem cells. Aggregates may be useful for the production of therapeutic proteins or other metabolic products of value. Aggregates may be useful for their metabolic capabilities to produce a valuable compound or molecule. Aggregates may be useful for the removal, inactivation or detoxification of molecules. Aggregates may be useful for the production of viruses, disabled viruses or recombinant viruses for use as vaccines or for use as gene transfer agents with applications in gene therapy. Aggregates may be useful as biosensors or diagnostic devices to detect certain compounds and molecules. Aggregates may be useful as a food product. Aggregates may be useful as a detection device to measure the toxicity of molecules or nanomaterials.

In another embodiment the invention includes a method of making a cell aggregation device composed of a biocompatible, cell-repellant polymeric hydrogel substrate comprising the steps of providing a negative replicate mold of the device of the invention, pouring a liquid solution of a biocompatible, cell-repellant polymeric hydrogel prepolymer into the mold, allowing the liquid solution to polymerize, and removing the solid hydrogel substrate from the mold.

In yet another embodiment, the cell aggregation devices and methods of the invention may be employed to construct encapsulated microarrays of aggregates of live cells for use in vivo or in vitro. Instead of employing current methods of encapsulation using alginate gelation via the formation of beads in a divalent cation solution, a novel technique to create microarrays of encapsulated aggregates was developed and is disclosed here. Encapsulation of the aggregates in situ on top of the biocompatible, cell-repellant polymeric hydrogel substrate that comprises the cell aggregation device allows for preservation of morphology of the wells, and the creation of an encapsulated, evenly spaced microarray sheet. Creation of sheets of encapsulated aggregates provides several advantages over the current cell encapsulation methods. Because an encapsulated microarray is larger than individual beads, a sheet can allow for a strong dose of directed delivery of signaling factors. Instead of injection of beads into the peritoneal cavity, a more directed insertion of the microarray could occur, allowing for a local delivery of drug. Encapsulated microarrays also allow for easy implantation and especially explantation if the device needs to be removed.

Thus, the invention further comprises devices and methods for encapsulating live cells. The cell encapsulating devices are composed of a biocompatible substrate having a substantially flat face and an opposed cell encapsulating face having at least one, preferably a plurality of spaced-apart, cell-repellant compartments recessed into the uppermost surface. Each compartment is composed of an upper cell suspension seeding chamber having an open uppermost portion and a bottom portion, and one, or more than one, lower cell aggregation recesses connected at the top to the bottom of the upper cell suspension seeding chamber by a port. The cell encapsulating microarrays of the invention are created from the cell aggregation devices of the invention, which are advantageously employed as a negative mold. Aggregated cells in the lower cell aggregation recesses of the aggregation device are encapsulated within the biocompatible, encapsulating substrate and then coated with a biocompatible coating layer as more fully described below.

The encapsulating substrate must be at least thick enough to support the cell-encapsulating compartments formed from the aggregation "mold" and not so thick that upon implantation, function is inhibited. Preferably the sheet has a thickness in the range of 100 to 1000 µl. The other dimensions of the sheet (length and width) may be highly variable depending upon the purpose intended for the device. Long, narrow sheets having spaced-apart cell-encapsulating compartments may be desirable for implantation of aggregates of chondrocytes to treat or repair cartilage defects. Sheets more or less square in dimension may be suitable for implantation of aggregates of epidermal cells to treat burns.

The spaced-apart, cell-encapsulating compartments extending from one of the surfaces of the encapsulating substrate must also be composed of biocompatible and bio-sustaining material. Preferably the compartments are an integral part of the substrate and formed of the same material, such that the substrate forms a unitary structure composed of a single, encapsulating material. The size of the compartments depends primarily on the dimensions of the substrate: the compartments may be any shape but must be small enough to be individually supported by the substrate and large enough to contain the desired number of aggregated cells. The substrate is preferably composed of crosslinked alginate, although other materials may be employed as long as they meet the following criteria.

One of the most important parameters for the functionality of the device is its ability to keep the aggregates within it alive. Accordingly, the substrate layer must be composed of a bio-sustainable material. By bio-sustainable we mean able to support the life of the aggregated cells for a period of time that allows them to execute the desired function. The material, for example an alginate substrate, must allow for diffusion of vital nutrients, growth factors and other molecules into the aggregated cells to sustain cell function, and also allow for waste products to diffuse out of the device. It must also permit the diffusion in of important molecules that might need to be metabolized or detoxified if the device is functioning in a metabolic capacity. Likewise, it must permit diffusion out of important molecules such as therapeutic proteins synthesized by the cell aggregates if the device is functioning in a delivery capacity. There are many adjustable parameters that can be made to the mechanics of alginate that will affect the strength and stability of the final device. One parameter is the actual composition of the material. Preferably alginate is used to make the substrate layer; and the relative concentration and molecular weights of guluronic to mannuronic subunits can be altered to create substrate layers with varying properties. Variations in the type of divalent cation used also can impact the relative stiffness and integrity of the substrate. High concentrations of guluronic acid give the casings of the substrate layer more mechanical strength while high concentrations of mannuronic acid sacrifice mechanical strength for coating affinity to produce a more stable uniform coating. Consideration as to method of implantation can also influence the composition of alginate. More elastic alginates may be optimal for implantation through injection while a more mechanically stable alginate will be desired for a surgical implant.

Although there are obvious advantages to having either high guluronic or mannuronic acid concentrations within the alginate, both properties of mechanical stability and affinity for coating material are important to the integrity of the microcapsules in vivo, and as a result, it has been empirically determined that an intermediate concentration of both subunits is optimal for biocompatibility and bio-sustainability.

The material must also be sterilizable and, if degradation is desired, capable of controlled degradation in response to biological conditions. In such case, the sterilizable, biodegradable polymer must have the requisite mechanical properties, must not induce inflammation or other toxic response, and must be metabolizable upon degradation. As the polymeric material degrades, the aggregated live cells become incorporated into the adjacent tissue, for example like a wound bed, and then the aggregates repair the wound. Thus, the device may also serve as a cell delivery system which is very easy to handle and drape over a site and since the device has a desired layout of the aggregates, the cells may be delivered to the site in a specific, desired geometry or configuration.

Alternative exemplary bio-sustainable materials that fulfill these criteria and may be employed for the substrate layer include collagen, PEG and hyaluronic acid and its derivatives, and agarose. Cross-linked polyacrylic acids, such as eudragid, may also be employed. Methods of crosslinking can be used including chemical cross-linking, and photopolymerization. Silicone or polyacrylamide hydrogels that are moderately hydrophilic may be used such as for example hydrogels of poly(ethylene oxide), poly(vinyl alcohol), polyvinylpyrrolidone and poly(hydroxyethyl methacrylate). Although the majority of hydrogels for biomedical purposes are made of synthetic polymers, hydrogels formed from crosslinked natural polymers, mainly polysaccharides, are well known and may be employed. Additional exemplary polymers are reviewed in Katz, "Biomaterials: Developments in Medica; Polymers for Biomaterials Applications," Medical Device & Diagnostics Industry, 122 (2001) and are discussed in Kalorama Information Industry Report: "Advanced Polymers for Medical Applications: Materials, Product Development, and Market Opportunities," Chapters 1 and 2 (2002).

The encapsulation device further comprises a coating layer composed of a biocompatible polymer that either completely surrounds the substrate and the cell-encapsulating compartments or substantially surrounds the cell-encapsulating compartments alone so as to impart additional stability to the substrate and ensure complete encapsulation of the aggregates. The coating layer is preferably composed of poly-L-lysine (PLL) and has a thickness in the range of 1-50 microns. Alternative coating layer materials include for example PLGA (polylactic co-glycolic acid), polyethylene imide, chitosan, and other positively charged biocompatible polymers. The selection of the appropriate coating material for use in the device of the invention is within the level of skill in the art.

Depending on the thickness of the coating layer and the thickness and chemical composition of the substrate, the encapsulation device can restrict passage in and out of large molecules and factors, and can retard the diffusion of other signaling factors. As a result, the selection of the thickness for both the substrate layer and the coating layer must take into account the intended use of the device and the size of the proteins, factors and the like which will be secreted by the aggregated cells. Multiple coatings are also possible as methods to impart strength and even drug release. An example of a multiple coating is the widely used APA system (alginate, PLL, alginate). Secondary coatings do not have to alternate and can be done with many chemicals as long as they will bind each other. Secondary coatings can also contain growth factors, drugs, or even cells and can be made of non-degradable or degradable materials. For example a two-stage device could be made where growth factors in the secondary coating are released over the short-term followed by growth factors synthesized and released by the cells over the long-term.

Engineering of alginate with additional polymers such as PEG not only provide stability to the device as a whole, but can also help in directing the release profile. Many drugs must be given in excess because they are rapidly cleared from the body before taking effect on the target tissue. Diffusion of the drug to healthy tissue also has an adverse effect on it and can cause significant side effects. By optional incorporation of a less porous backing layer on the device, diffusion of the desired factor can be restricted on one face of the sheet, driving the concentration towards the face that is closer to the target tissue, allowing for a stronger effect. Although diffusion through the back of the device cannot be completely controlled, it can be controlled and limited so that a more even and stronger release is observed preferentially on once face. This polarity can also be useful for the preferential delivery or metabolic activity of the device for use in the in vitro bioreactor applications.

In another embodiment, the device is composed of a substrate comprising a substantially flat sheet of material from which the cell-encapsulating compartments extend from one face or side at more or less regular intervals in a microarray and a coating layer coating the cell-encapsulating compartments, and being composed of the same material as the substrate and having a thickness sufficient enough to form a substantially flat sided sheet on the cell-encapsulating side of the device. In this embodiment the device would have two substantially flat surfaces. It is envisioned that such a "double flat" device would not require a separate coating layer. However, a coating layer may be desired in order to further improve the mechanical properties of the device or to generate a directional diffusion of factors, nutrients and the like. Moreover, the coating layer could itself contain one or more biological substances, for example cell modulating factors (growth factors, inhibitory factors etc), to assist in modulating the encapsulated cells, provide additional nutrients to the cells or to affect the drug delivery process.

In another aspect the invention comprises a method of making encapsulated, aggregated live cells comprising the steps of depositing a plurality of cells into an upper cell seeding chamber of the cell aggregation device that is being employed as the negative mold, incubating said cells for time sufficient to allow the cells to aggregate, depositing the aggregate-encapsulating substrate material into the upper cell seeding chamber, curing the substrate to form the aggregate-encapsulating substrate layer, removing the substrate layer from the mold and immersing the substrate layer in a solution of the biocompatible polymeric material to form the coating layer. Optionally, as exemplified in Example 10, the dynamics of cellular aggregation can be controlled by the administration of selected aggregation modifying agents (as discussed above) prior to the incubation step.

In another embodiment cells may be deposited into the seeding chamber while suspended in the un-cured encapsulating substrate material, incubated until the cells aggregate and then the substrate cured. Cells may also be deposited into the device's seeding chambers after a small amount of the encapsulating material has been added and crosslinked inside the seeding chamber. After addition of the cells or a suspension of cells and encapsulating material, additional encapsulating material can be added, followed by a cross-linking step.

The method of making the devices of the invention results in microarrays that are more uniform, predictable and regular that the current alginate beads. The precise location and number of cells per aggregate can be controlled, resulting in a more uniform and predictable release of the therapeutic. Because spacing and configuration is controllable, diseased tissue can be treated uniformly or differentially as needed. Body fluid flow across the top of the sheet will allow for quick and effective clearance of factors from the immediate vicinity of the device onto the target tissue. Because the distance the factors would have to travel are small, there is less worry of clearance by quenching the factor or loss through the bloodstream. Furthermore, because of the ability to place the microarray directly on the diseased tissue, intense localized delivery of therapeutic factors can be achieved. Cells can produce therapeutic factors either continuously through genetic alteration of the cell's genome, or through a response pattern, reacting to the environmental cues it is given to selectively modify the rate and amount of production of therapeutic factors. By implanting an array of encapsulated aggregates, a more even distribution and diffusion of the desired factor is achieved, eliminating the nodes of high factor concentration that are consistently found around alginate microcapsules.

Commercial and scientific grade alginate and PLL can be purchased through a variety of companies in various molecular weights. For purposes of understanding the influence of composition of both polymers on the molecular level, characterization is essential. Through nuclear magnetic resonance (NMR) and differential scanning calorimetry (DSC), both composition and makeup of both alginate and PLL can be determined. DSC is especially useful for analyzing the ratio of guluronic to mannuronic acid in the alginate. Analysis of the entire microarray through DSC confirms the presence of PLL coating, seen in a third peak for its glass transition temperature. Because DSC uses dried samples, there is the potential of measuring a heat profile that could be misleading with respect to the actual device. Although a hydrated microarray could be used, the profile for water that would be seen in the resulting graph would make it hard to determine the makeup of the polymer.

The ability of the microencapsulated arrays to remain in vivo without fracture can be assayed in two phases, in vitro and in vivo. For the in vitro steps, devices are kept in normal media for an extended period and observed daily for fractures, stress to the device or contamination. Under a set time course, this establishes the base-line durability level of the microarrays in an environment that mimics serum. Next, implanting the device in an animal model, with explantation at time points corresponding to those set in vitro is undertaken and the implanted microarray is observed for fracture and general stability. The same set of experiments is done with mixtures of different polymers, for example, a combination of alginate and PEG.

Transfected cells should be screened and selected for before aggregation. Ability to secrete the desired factors should be confirmed through assays in vitro before and after aggregation. Once aggregates are encapsulated, their ability to secrete therapeutic factors is complicated by the porosity of the alginate matrix. Factors must be able to diffuse through the alginate matrix to be effective and aggregation modifying agents must be able to diffuse through the matrix. This can be measured by placing the device in a diffusion chamber, and measuring the concentration of factor diffused through the device during a set time course. To further validate this effect, a flow could be applied through the chamber to facilitate clearance of the factor while more accurately mimicking environmental stresses that the device may encounter in vivo.

In vitro fluid modeling can be employed to characterize the microarray. Modeling release patterns employing computer algorithms could provide insight as to how the microarray would function in vivo. Instead of a periodic diffusion where there would be high concentration of therapeutic factor close to the alginate bead, and decreasing amounts further away, we anticipate that the microarray device of the invention will smooth out the nodes of factor concentration. By juxtaposing two similar release patterns, more therapeutic factor is more evenly dispersed over the area, potentially increasing the range of effect while maintaining even dosage. Arrays of a large number of aggregates, and the release profile over the disease region to which the sheet is grafted will be nearly even, allowing for even dispersion and even effect throughout the damaged organ or tissue.

The encapsulated aggregated cells may be used in research, in tissue engineering applications such as cell transplantation, in functional micro-tissue formation, or in bioreactor applications. The encapsulated aggregated cells may be used for the production of therapeutic proteins. The device may be employed to retrieve products, for example secretory proteins, to introduce biochemical stimuli and to create three-dimensional biochemical gradients.

One of the most important benefits of cellular encapsulation is the ability to transplant cells into the host without worrying about the host immune response. Because of the mechanical protective barrier of alginate-PLL, or alginate alone, physical contact between macrophages and other immune cells is impossible. Furthermore, the pores in alginate function as a selectively permeable membrane that allows only small proteins and molecules in while preventing larger, more complex molecules such as immunoglobins access to encapsulated cells. See Jones et al., *Transplantation* 78: 1454-62 (2004) and Zimmerman et al, *J. Mat. Sci.* 16: 491-501 (2005).

To characterize the immune response, an in vivo implant can be followed throughout a time course similar to the one used to assess the device's structural integrity. Sections of the alginate device can be and fixed and stained to determine the presence of immune cell overgrowth on the periphery of the device, and physical examination of the animal can provide evidence as to the level of inflammation in the area where the device is implanted. Overgrowth is promoted by surface irregularities but is typically only found in approximately 5% of cells encapsulated with the current bead technology. See De Groot et al., *J. Surgical Res.* 115: 235-41 (2003) and De Groot et al., *J. Surgical Res.* 121: 141-50 (2004). A similar in vitro experiment can be conducted to characterize the immune response to the microarrays of the invention.

Normally encapsulated cells are delivered via a subcutaneous injection or injection into the peritoneal cavity. Because of their small size and tendency to disperse, they cannot be explanted. Furthermore, there is the risk of microcapsules being formed with less than smooth coatings or alginate matrices around them which would recruit and cause overgrowth of capsules by macrophages. With the microarrays of the invention, a more directed implantation procedure is possible. If treating a disease specific to a certain organ or tissue location in the body, the microarray sheet can be grafted or placed directly on top of the problem, allowing intense, localized drug delivery. In the event of contamination, immune rejection or planned removal the device can be explanted.

In yet another aspect the invention comprises encapsulated, aggregated live cells made by the foregoing method of the invention. Virtually any type of cells may be aggregated and encapsulated using the device and method of the invention; there are no particular limitations with regard to the cells that may be employed, as long as the cells have the ability to aggregate (some cells, such as mature red blood cells and fully mature spermatozoa are not known to be able to aggregate). The cells may be prokaryotic or eukaryotic. Any type of mammalian cells, for example mice, rat, primate (especially human primate), chicken, porcine, bovine, equine cells, may be used. Either primary cultured cells or an established cell line can be employed. The primary cultured cells may originate from any tissue, e.g. cartilage, bone, skin, nerve, oral. alimentary canal, liver, pancreas, kidney, gland, heart, muscle, tendon, fat, connective, reproductive organ tissue, ocular, blood vessel, bone marrow and blood. Exemplary cell types include osteoblasts, keratinocytes, melanocytes, hepatocytes, gliacytes, pancreatic beta cells, pancreatic exocrine cells, neural stem cells, neural precursor cells, spinal cord precursor cells, nerve cells, mammary gland cells, salivary gland cells, renal glomerular endothelial cells, tubular epithelial cells, adrenocortical and adrenomedullary cells, cardiomyocytes, chondrocytes, skeletal and smooth muscle cells, fat and fat precursor cells, corneal and crystalline lens cells, embryonic retina cells, vascular cells, endothelial cells, bone marrow stromal cells and lymphocytes. For example, the device and method of the invention may be employed to aggregate muscle cells (smooth, skeletal, cardiac), connective tissue cells (fibroblasts, monocytes, mast cells, granulocytes, plasma cells, osteoclasts, osteoblasts, osteocytes, chondrocytes), epithelial cells (from skin, gastrointestinal, urinary tract or reproductive tract, or organ epithelial cells from the liver, pancreas or spleen), or nervous system cells (glial, neuronal, astrocytes).

Additionally, encapsulated aggregates of mammalian stem cells (embryonic, non-embryonic and hematopoietic) may be produced using the device and method of the invention. Upon aggregation, the stem cells form an "embryoid body". After a few days the aggregate forms a cystic embryoid body (essentially a hollow ball) and internal structures, for example a yolk sac or cardiomyocytes. The stem cell aggregates may be from differentiated stem cells, i.e. those with a distinct cell lineage prior to aggregation, or the stem cells may undergo differentiation in the cell aggregate after or during aggregation. Differentiation results in cells that have specific functions. Undifferentiated cells are pluripotent, i.e. they have not yet developed their specific function. Exemplary are stem cells of all types: ectodermal, mesodermal, endodermal, mesenchymal, hematopoietic, neural, hepatic, muscle, pancreatic, cutaneous, retinal and follicular stem cells.

Non-mammalian cells from any non-mammalian organism may also be used in the device. Numerous plant cell lines, animal cell lines, insect cell lines, plant virus cell lines and cells lines of microorganisms (such as Archaea, bacteria, plasmids, phages, yeasts and fungi exist) are available from repositories known to those of skill in the art. (DSMZ, the German National Resource Centre for Biological Material is one; ATCC, the American Type Culture Collection is another.) Cells from any of the known respositories may be advantageously aggregated using the device and method of the invention.

The cells to be aggregated and optionally encapsulated using the devices and methods of the invention may be native cells or genetically modified cells or mixtures thereof. Genetic modification to alter cellular RNA or DNA by addition, deletion or substitution is a well known technique in the art. One type of cells may be used or a combination of cell types may be used. Normal cells or abnormal cells may be aggregated in the device of the invention. Mixtures of normal and abnormal cells may be employed. Neoplastic or cancerous cells may be employed, such as for example, MC3T3-E1 cells that differentiate into osteoblasts and MC3T3-G2/PA6 cells that differentiate into fat cells. Any of the eleven SUM breast cancer cell lines that are well characterized and represent different subtypes of breast cancer including 44PE, 52PE, 102PT, 149PT, 11315MO2, 159PT, 185PE, 190PT, 225CWN, 229PE and other breast cancer cell lines including MDA-MB-435S, MDA-MB-231, MCF7, SK-OV-3, BJMC3879, MCF-7, MDAMB361, MFM223, BT549, MDAMB468, T-47D, BT474, SK-BR-3, HS578T can be used. Any of the prostate tumor cell lines including OPCT-1, OPCT-2, OPCT-3, DU145, LNCaP and PC-3 can be used. Any of the lung cancer cell lines including A549, NCI-H460, NCI-H1299 can be used. Any of the colon cancer cell lines including HCT116, HCT116p21−/−, HCT116p53−/−, HCT-15, HT-29, CaCo-2, CoLo205, SW48 can be used. Any of the skin cancer cell lines, including for example SK-MEL-28, SK-MEL-5, SK-N-SH, HT1080, P815, SW872, UMSCC-14A, KS SA1N, UACC903 and A-431, can be employed. Any of the brain cancer cell lines, including for example IMR-32, U-87 MG, A172, N1E115, SHSY5Y, A20, Neuro2A (N2a), SKNSH, C6, PC12, and U87, can be used. Any of the kidney cancer cell lines, including for example 786-O and ACHN, can be used. Any of the liver cancer cell lines, including for example HepG2, COLO 587, FaO, HTC and HuH7, can be used. Any of the bone cancer cell lines, including for example U-2OS, can be used. Any of the ovarian cancer cell lines, including for example A2780, DOV13, OVCAR3, CoLo357 and HeLa, can be used. Any of the pancrease cancer cell lines, including for example Capan1, Panc1 and Panc89, can be used. Any of the adrenal cancer cell lines, including for example H295R and SW13, can be used. Any of the bladder cancer cell lines, including for example ECV304, can be used. Any of the bone/cartilage cell lines, including for example SAOS2, SW1353 and U2OS, can be used. Differentiation-inducing factors may be added to the cells before, after, or as part of, encapsulation. Such factors are known in the art; exemplary factors include for example stem cell growth factors, interleukins, interferons, tumor necrosis factors, colony stimulating factors, erythropoietin and thrombopoietin, insulin, indomethacin, dexamethasone and transferrin. Other agents, peptides, drugs or molecules can be added to promote or guide differentiation down certain pathways such as inhibitors of kinases, agonists or antagonists of receptors or interfering RNA or antisense oligonucleotides. The differentiated cells may then be employed in therapeutic methods. Alternatively, after aggregation of undifferentiated cells, the aggregates may be induced to differentiate upon transplantation into an animal.

Heterotypic encapsulation devices may be made and employed. For example, one cell type that is transfected with a desired gene and another cell type that is known to secrete immunosuppressants may be aggregated in different compartments of a multi-compartment aggregation device and encapsulated with the biocompatible encapsulating substrate layer and the coating layers as described. Alternatively, both cell types could be aggregated together or sequentially in the same compartments or different layers depending on the device Composition. Localized immunosuppression in the vicinity of the device could be provided by either a heterotypic aggregate containing Sertoli cells, enucleated erythrocytes or by transfecting target cells in the aggregates to be resistant to the influence of NO and other small immunogenic factors. Successful incorporation of Sertoli cells can create a localized area of immunosuppression that will aid in the dynamic delivery of the desired therapeutic factors while protecting the device integrity without requiring a lifelong regimen of dangerous immunosuppressants for the patient. Cells known to be immunosuppressants may become a stable co-encapsulated cell that provides local immunosuppression to prevent array overgrowth while maintaining the systemic immune system. Sertoli cells and erythrocytes are exemplary. See Ramen et al., *Transplant International* 18: 1001-1009 (2005) and Wiegand et al, *Transplantation* 56:1206-1212 (1993).

The encapsulated aggregated cells may be employed alone or in combination with known tissue transplantation scaffolds to replace or augment damaged tissues and organs. For example, islet-like encapsulated aggregates made using the device of the invention may be employed in the treatment of diabetes, encapsulated dermal papilla cell aggregates may be employed to treat baldness, encapsulated hepatocytes aggregates may be employed in the treatment of liver disease, encapsulated dermal cell aggregates may be employed in cosmetic and reconstructive treatments of the skin and encapsulated chondrocyte and/or osteoblast aggregates may be employed in articular cartilage repair.

Encapsulated aggregates of cancer or precancerous cells may be transplanted into laboratory animals to study tumor growth, metastasis, and treatment. Encapsulated aggregates may also be used in the areas of high throughput drug screening and personalized medicine to measure drug efficacy or toxicity. Encapsulated aggregates may be used to investigate or direct the differentiation of stem cells. Encapsulated aggregates may be useful for the production of therapeutic proteins or other metabolic products of value in vitro and in vivo. Encapsulated aggregates may be useful for their metabolic capabilities to produce a valuable compound or molecule. Encapsulated aggregates may be useful for the removal, inactivation or detoxification of molecules or in the production of viruses, disabled viruses or recombinant viruses for use as vaccines. Encapsulated aggregates may be employed as gene transfer agents with applications in gene therapy. Encapsulated aggregates may be useful as biosensors or diagnostic devices to detect certain compounds and molecules. Encapsulated aggregates may be useful as a food product. Encapsulated aggregates may be useful as a detection device to measure the toxicity of molecules or nanomaterials. Encapsulated aggregates may be useful in the fabrication of bioreactors.

The encapsulated microarray of aggregates may be employed to deliver drugs that are harmful to the body in the large concentrations that are used because of their short half lives. Current barriers to treatment of cancers with factors like IFN-γ, TNF-α, -β, and -γ and endostatins result from the toxicity of these molecules due to concentrations required to result in a beneficial effect. However, cells can be transfected with a gene cassette that will produce endostatins on a dose response basis. See Joki et al., *Nature Biotechnology* 19: 35-39 (2001); Read et al., *Nature Biotechnology* 19: 29-34 (2001). Such cells can then be aggregated, encapsulated and implanted within or onto the tumor site, allowing for a sustained, concentrated delivery of immunogenic factors that are known to kill cancer cells.

Other features and details of the invention are particularly described in the following examples. The examples are intended to illustrate the features of the invention without limiting its scope to the details described in them.

DETAILED DESCRIPTION OF THE DRAWINGS

Figures 3A, 3B, 3C, 3D:
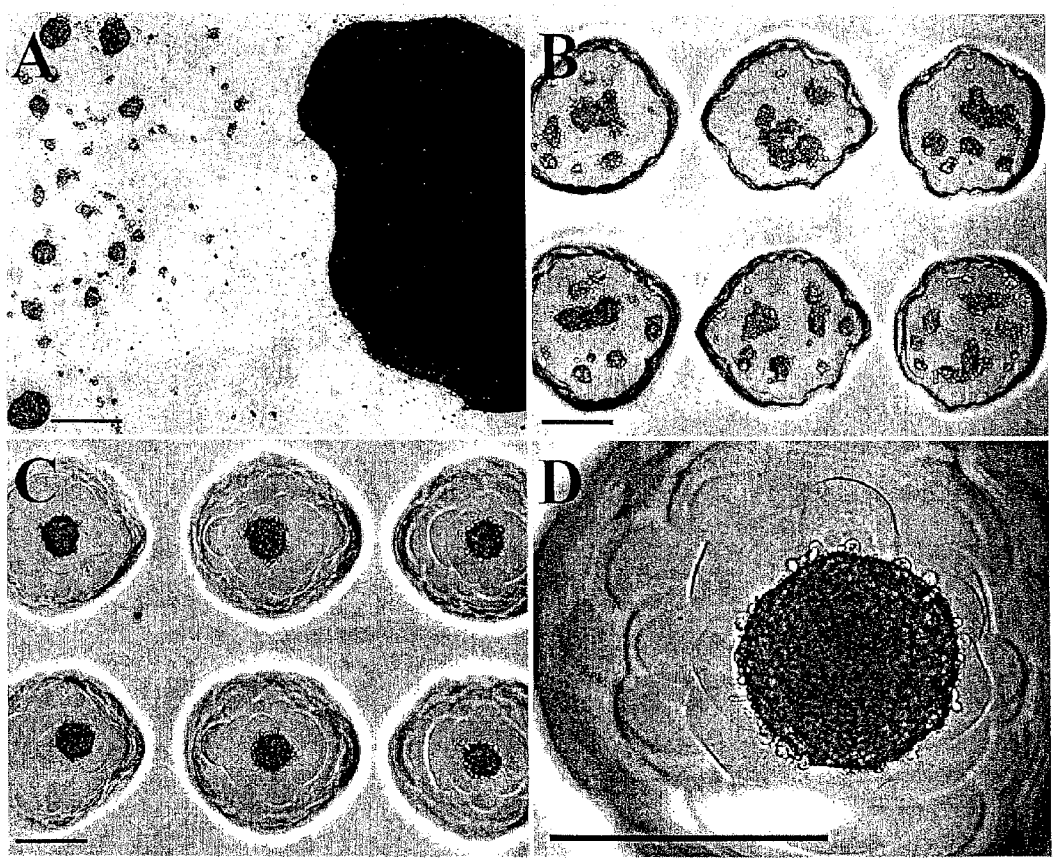

FIG. 3 is a copy of a photographic reproduction showing the results of controlled cellular aggregation using a device of the invention made as described in Example 1. FIG. 3A shows aggregation of normal human fibroblast cells on a single large flat recess. FIG. 3B shows aggregation in flat-bottomed 400 μm diameter recesses. FIG. 3C shows aggregation in hemispherically-shaped 400 μm diameter recesses. FIG. 3D is a high magnification of a single spherical aggregate of cells in one of the recesses of FIG. 3C. The scale bar=300 μm.

Figure 4:
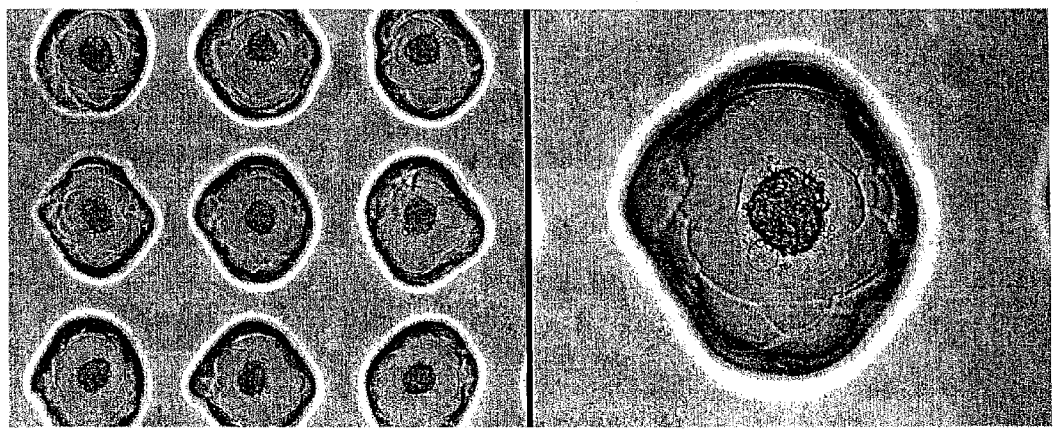

FIG. 4 is a copy of a photographic reproduction of the results of Example 2 which shows a plan view of the array of aggregates of fibroblast cells in 400 micron diameter aggregation recesses and a close up of one of the aggregates of fibroblast cells in a single recess.

Figure 5:
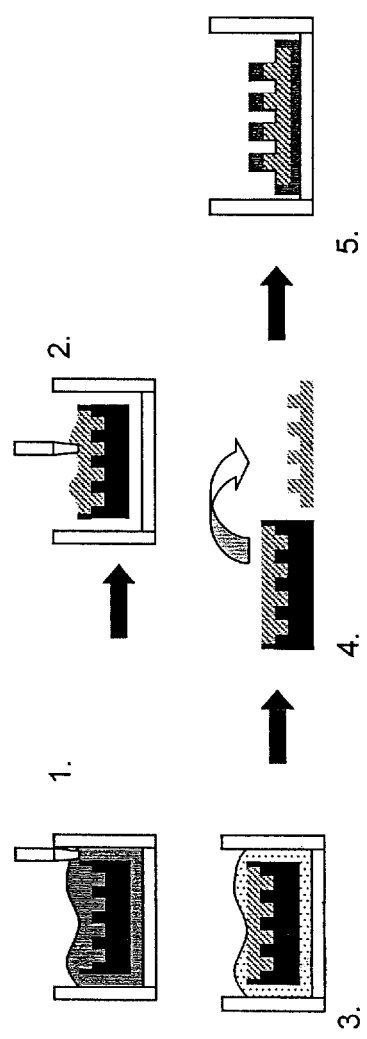

FIG. 5 illustrates the method of fabricating the encapsulated aggregated live cells of the invention, as described in detail in Examples 6 and 7.

Figure 6:
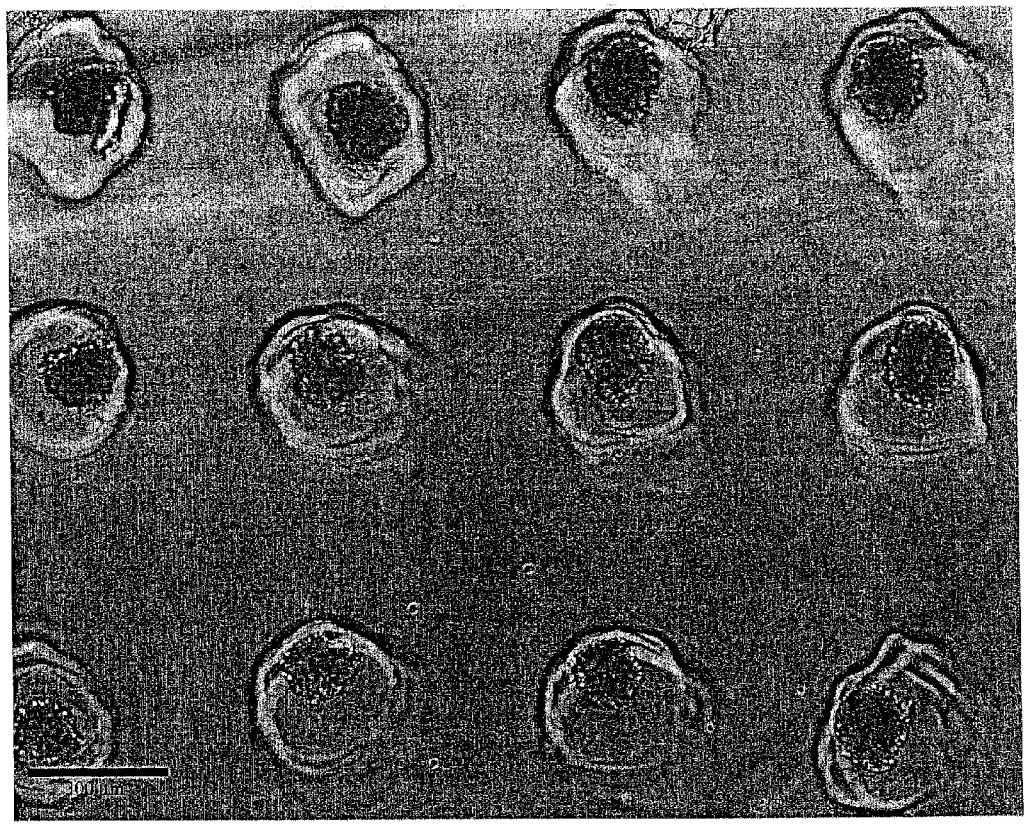

FIG. 6 is a copy of a photographic reproduction of the microarray of aggregated cells encapsulated in 1.8% alginate solution. After drying, the microarray was peeled off the acrylamide cell aggregation device and aggregates were observed with the features. Scale bar 300 μm.

Figure 7A:
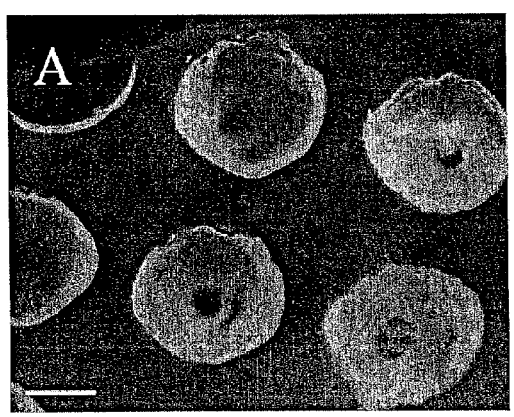
Figure 7B:
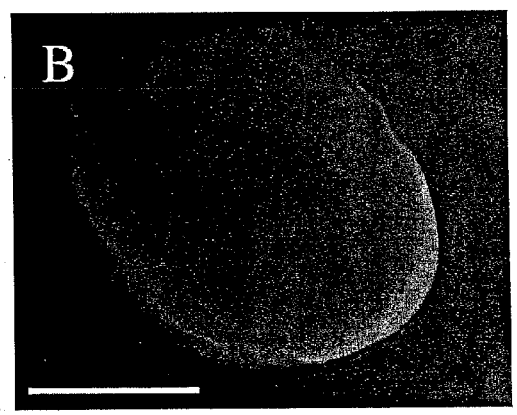

FIGS. 7A and B are graphic illustrations of the results of the self-assembly experiment described in Example 9A.

Figures 8A, 8B, 8C:
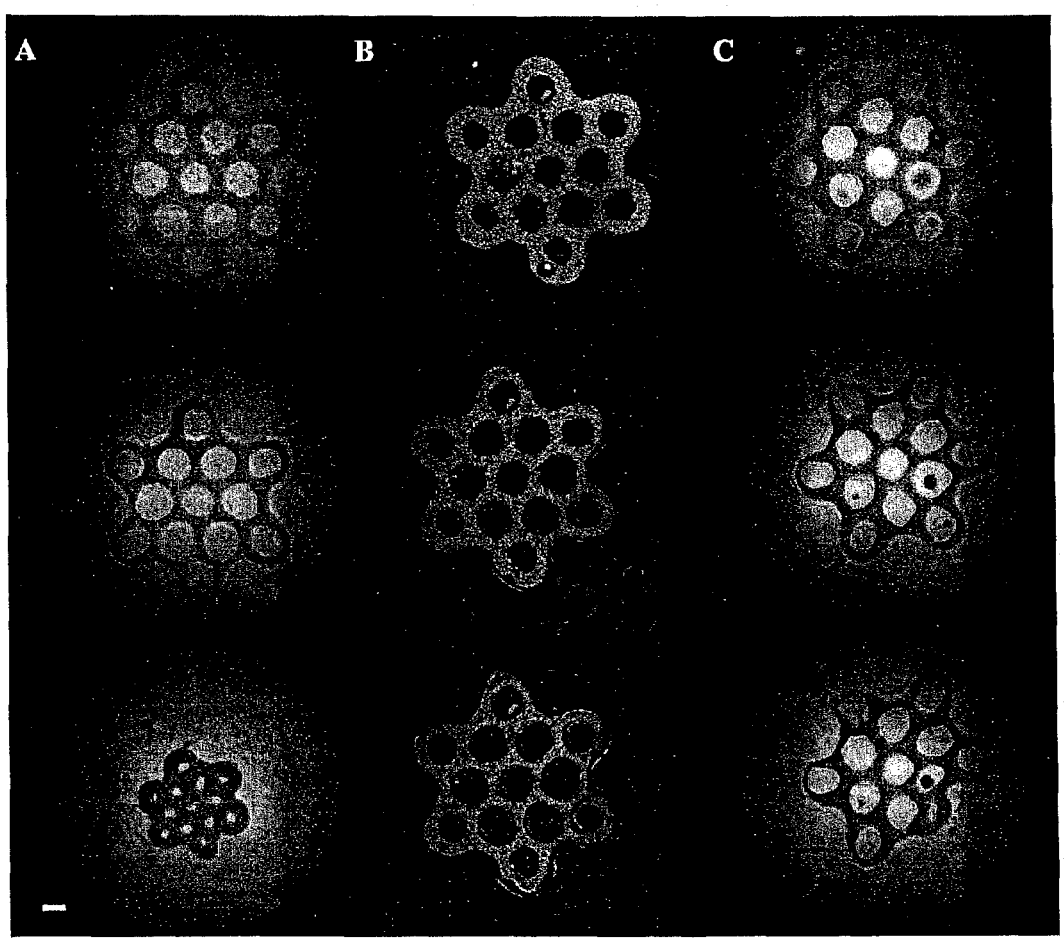

FIGS. 8A-C are a photographic reproduction of the results of the time-lapse experiments using honeycomb-shaped recesses in the cell aggregation devices, as described in detail in Example 9B.

Figure 9:
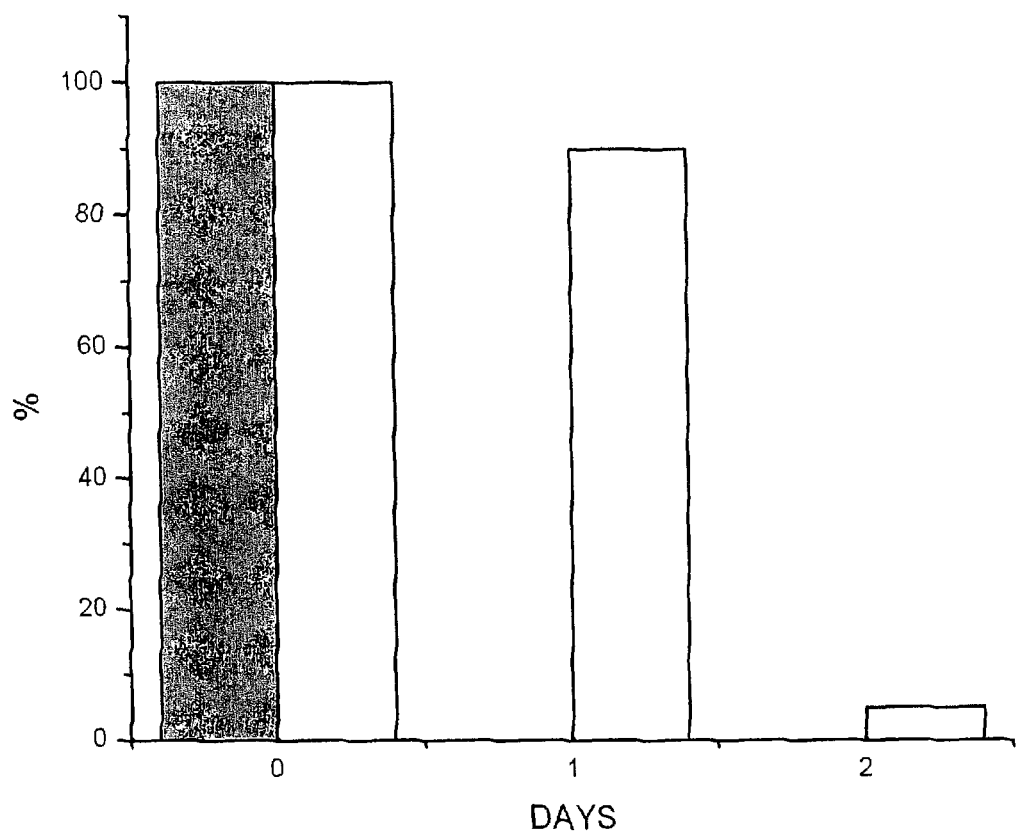

FIG. 9 is a histogram showing the results of the aggregation experiments done using micro-molded agarose toroidal aggregation devices seeded with untreated NHFs or NHFs treated with an aggregation modifying agent, as described in Example 10.

Figure 10:
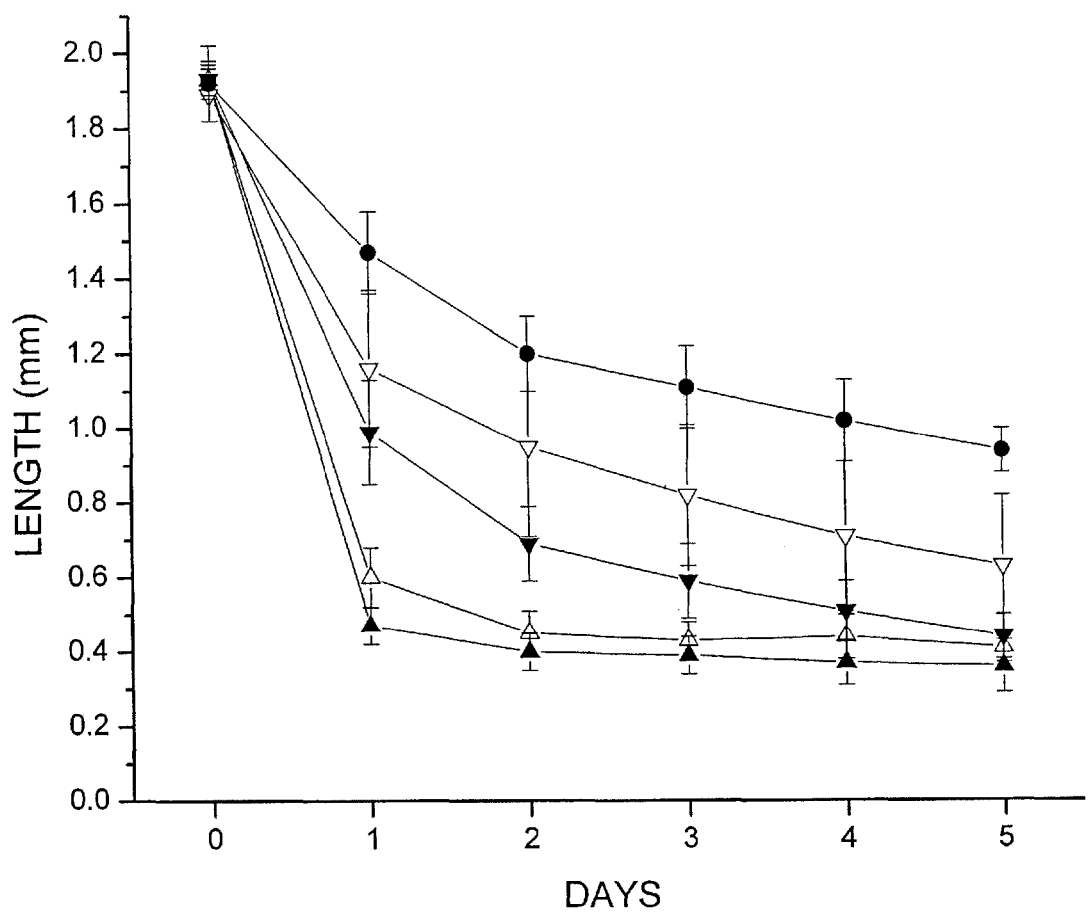
Figure 11:
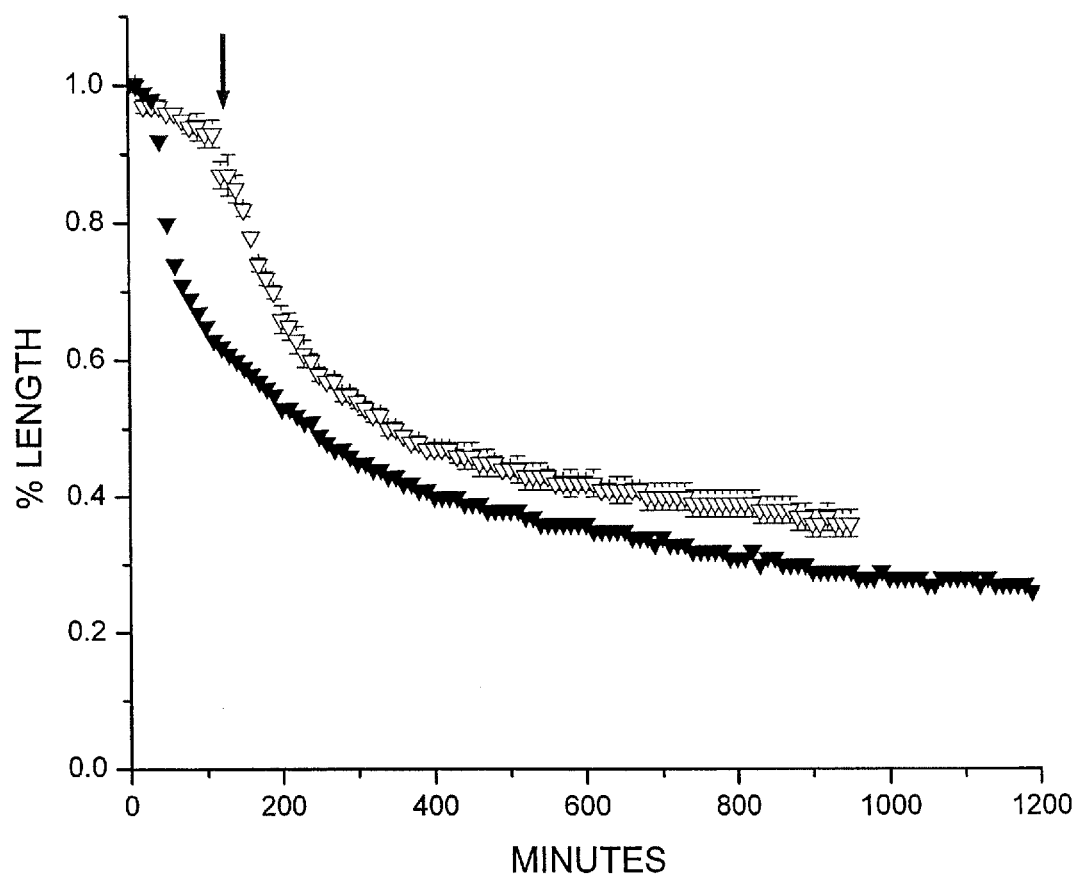

FIGS. 10 and 11 are graphic representations of the results of the drug-assisted aggregation experiments using the aggregation devices of the invention having trough features, as described in Example 10.

Figure 12:
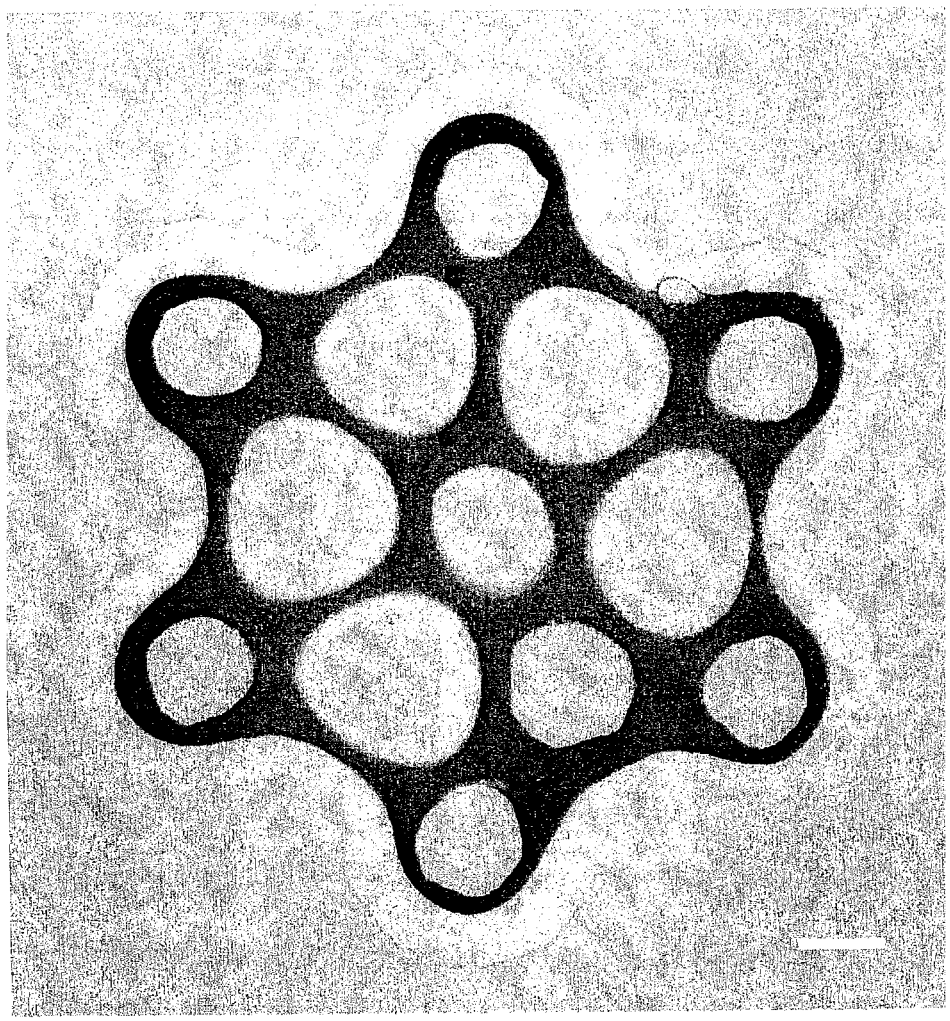

FIG. 12 is a photographic reproduction of some of the results from the drug-assisted NHF cell aggregation experiment using honeycomb-structured cell aggregation devices of the invention.

EXAMPLES

Example 1

Cell Aggregation Device Fabrication and Cell Culture Preparation

Figure 1:
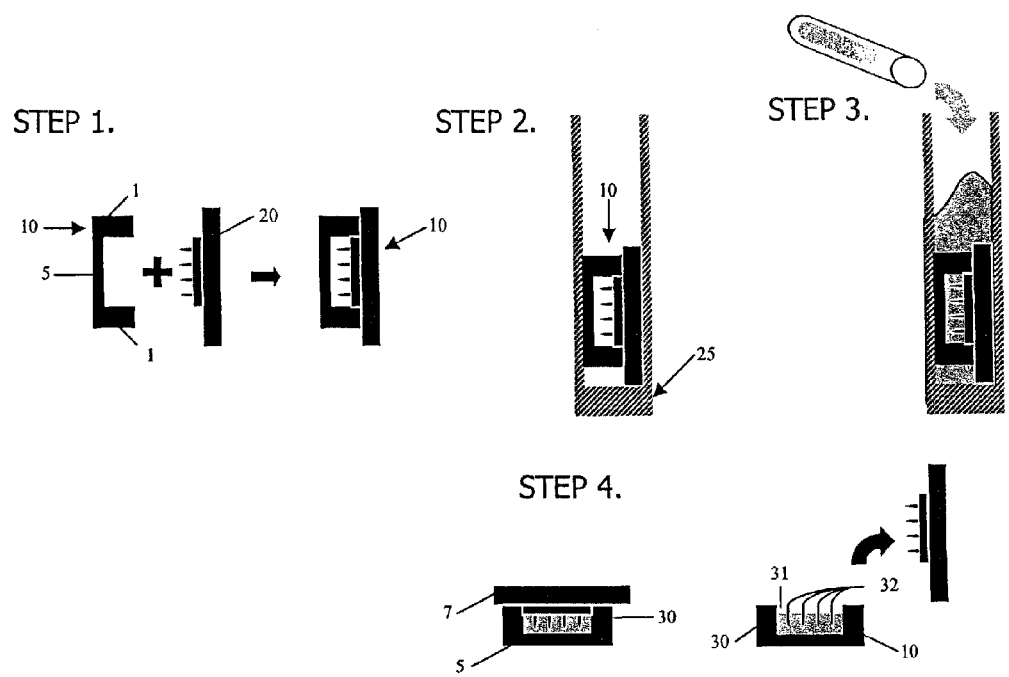
FIG. 1 illustrates the four step fabrication method of the cell aggregation device of the invention in general.

The fabrication method is illustrated for a general device of the invention in FIG. 1. Thirty millimeter Millicell® CM cell culture inserts 10 (Millipore), which are essentially rigid plastic rings 1 having porous polytetrafluoroethylene (PTFE) membranes 5 on their bottoms, were employed as mold templates. The PTFE membrane, which is transparent when wet, permits diffusion of culture media and visualization of cell aggregates through an inverted microscope. AutoCAD 2005® software was employed to design the shape and contours of various cell aggregation devices and polyacrylamine substrates were made from the wax templates by rapid prototype printing of sequential layers of wax to create the desired 3D CAD designed topography. Mold topography was designed such that gravitational force could funnel cells into the aggregation wells. The wax template was designed to produce a flat square recess 1 mm in depth from the top of the mold. The created software files were fed into a 3D Systems ThermoJet® rapid prototyping machine for mold manufacture.

Once the molds were made, hydrogel casting was performed with a multiple mini-vertical gel casting chamber Model #Gcc-210 from C.B.S. Scientific. In the biological safety cabinet, six 30 mm Millicell® CM cell culture inserts 10 were snapped onto six wax molds 20. The assembly was placed in a vertical gel casting chamber 25 so that the composite was oriented vertically between 2 glass plates (step 2 in FIG. 1) and the bottom of the gel casting chamber. 100 ml of 15% pre-polymer solution was prepared by mixing 37.5 ml of acrylamide/bisacrylamine (29:1 mix ratio, 40% solution; Sigma-Aldrich A-7802) with 31.25 ml of Tris buffer, pH 6.8, and 31.25 ml DMEM (1% penicillin/streptomycin) in two 50 ml conical centrifuge tubes. The pre-polymer solution was degassed by exposure to vacuum for 30 sec., capped and transferred to a chemical fume hood. In the hood, 500 µl of initiator, 10% APS (ammonium persulfate solution in deionized water; Sigma-Aldrich A-9164) and 100 µl of TEMED (N,N,N,'-tetramethylethylenediame 99%; Sigma-Aldrich T-7024) catalyst was added to the 100 ml of pre-polymer solution, mixed by inversion and transferred to the biological safety cabinet for gelation.

In step 3, about 75 ml of the mixture was pipetted into vertical gel casting chamber 25 to fill the spaces between molds 20 and inserts 10. The remaining approximately 25 ml was left in a capped centrifuge tube as a tester to confirm polymerization. Because the PTFE membranes, 5, were porous, the solution flowed into the pores and polymerized, which tethered the hydrogel to insert 10 at membrane 5. After 2 hours polymerization was complete and the assembly was removed from casting chamber 25 by disassembly of the chamber in the hood using aseptic technique. Excess polymerized hydrogel was cut away from around inserts 10, wax molds 20 were removed and inserts 10 now supporting the polyacrylamine hydrogel cell aggregation device 30 were transferred to sterile 6-well tissue culture plates. Cell aggregation device 30 can be seen in FIG. 2 comprised of cell suspension seeding chamber 31 and a plurality of cell aggregation recesses 32. The volume of cell suspension seeding chamber 31 directly above aggregation recesses 32 was about 300 µl.

The foregoing is the preferred method for cells that are to be aggregated and encapsulated in alginate. Otherwise, a simplified procedure is preferred in which the PTFE mold templates are not employed and the devices of the invention are cast from a polydimethylsiloxane (PDMS), or functionally equivalent polymer, instead of wax. For example, a PDMS mold having the appropriate dimensions and structures is cast and molten agarose solution (2-4% w/v in water) is added to the mold and allowed to cool. Once cooled, the agarose can be removed from the mold, yielding a hydrogel that is an exact negative replicate of the PDMS mold. Various sized molds may be created to fit several standard sized tissue culture plates. To maintain sterility, the protocol is performed in a biological safety cabinet using autoclave-sterilized agarose solution and PDMS molds. This is the preferred method of making the devices of the invention when the aggregated cells will not be encapsulated in alginate.

Example 2

Figure 2:
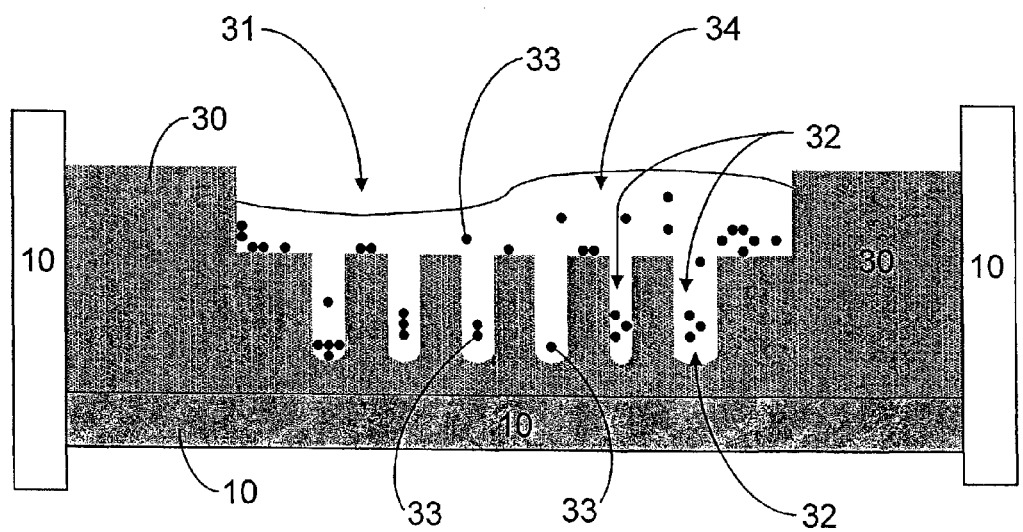
FIG. 2 is a cross-section view illustrating one embodiment of the device of the invention showing one cell suspension seeding chamber and six cell aggregation recesses.

Cell Seeding and Aggregation of Human Diploid Fibroblasts 3 ml of cell culture media (DMEM supplemented with 1% penicillin/streptomycin as antibiotic, with and without fetal bovine serum) was added to and the plates transferred to a cell culture incubator and allowed to equilibrate overnight to rinse out any unreacted monomer, neutralize pH and fill the pores of device 30 with the media. In a biological safety cabinet, excess media was aspirated out of the 6-well tissue culture plates. Normal human diploid fibroblast cells were trypsinized, counted and resuspended to a cell density of 1.67 million cells per ml. 300 µl (i.e., about 500,000 cells) were pipetted into each seeding chamber. FIG. 2 illustrates the cells 33, in various stages of the process of entering the aggregation recesses 32, are shown bathed media 34, just after being pipetted into one of the seeding chambers.

The hydrogel cell aggregation devices were transferred to the incubator for about 1.5 hours to allow cells to settle into the cell aggregation recesses and then transferred to a biological safety cabinet and to each well of the 6-well tissue culture plates was added 3 ml of additional media by slow pipetting onto an inside wall of the well so as not to disturb any cells. The devices were then returned to the incubator and allowed to stand. After 24 hours cell aggregates had formed and were retrieved by inverting the devices within the wells of the 6-well plates (that still contained about 3 ml media) for 5-10 minutes. The yield was between 80-90%. Mild centrifugation after inversion (5 minutes, 25° C., at 500 rpm) increased the yield to 100%. Light microscope images were taken during the 24 hour incubation period, at times t=0, 1, 2, 10 and 20. The results are shown in FIG. 4, which is a copy of the photographic image taken from above (plan view) of the array of fibroblast cell aggregates in 250 micron diameter aggregation recesses and a close up of one fibroblast cell aggregate in a single recess. Cell aggregation could clearly be seen after 2 hours (data not shown) and the cells are completely aggregated at 20 hours as shown in FIG. 4.

Controlled aggregation within the device requires a cell-repellent surface that is shaped to funnel cells together. This combination of surface properties and geometry acts to increase intercellular interaction and cell adhesion. In this example the effect of geometry on aggregation was evaluated; cells were seeded onto cell-repellent polyacrylamide gels with various topographical features. Devices containing cylindrical recesses with a diameter of 400 µm with either flat or hemisphere-shaped bottoms were constructed. In addition, devices were constructed with a single large (17.6 mm×17.6 mm×1.8 mm) flat rectangular recess. These hydrogels were seeded with normal human fibroblasts ($2.5 \times 10^5$ cells per device). Photographic images taken 24 hours after seeding demonstrated that control of the aggregation process is improved by geometries that utilize gravity to funnel cells more closely together. As can be seen in FIG. 3A, the single large flat recess resulted in erratic and uncontrolled cell aggregation with irregularly shaped aggregates ranging in size from tens of microns to several millimeters. In the case of the 400 µm diameter recesses with hemisphere-shaped bottoms, cells formed a single spherical aggregate lying in the center of each recess as can be seen in FIG. 3C. In contrast, cells in the flat-bottomed 400 µm. diameter recesses formed multiple irregularly-shaped cell clusters scattered in each recess as can be seen in FIG. 3B. A single spherical aggregate formed in one of the recesses having the hemisphere-shaped bottom is shown in FIG. 3D.

Example 3

Aggregation of a Mixed Population of HUVEC and Fibroblasts

Human umbilical cord vascular endothelial cells (HUVEC) were seeded alone and simultaneously in co-culture with normal human diploid fibroblasts, the latter of which were also seeded alone. To visualize the different cell types, Cell Tracker™ fluorescent living cell stain was used. A freshly trypsinized suspension of HUVECs was incubated in 5 µM green fluorescent Cell Tracker™ (in cell culture medium) and a fibroblast suspension was incubated in 5 µM red fluorescent Cell Tracker™ for 45 minutes. Cell suspensions were centrifuged, Cell Tracker™ was aspirated off, and the cells were re-suspended in fresh media and incubated for 30 minutes.

Cell suspensions were then seeded into the seeding chambers of the aggregation devices made in accordance with Example 1 above. 0.50 million HUVECs alone (homogeneous population), 0.50 million fibroblasts alone (homogeneous population) and 0.25 million HUVEC and 0.25 million fibroblasts in co-culture (mixed population) were added to seeding chambers. The three populations of cells were allowed to aggregate for 2 days and then visualized using phase contrast as well as fluorescent microscopy. The homogeneous populations of fibroblasts or HUVECs formed aggregates within the aggregation recesses; and the mixed population of fibroblasts and HUVECs formed heterotypic aggregates within the aggregation recesses. In the mixed population, fibroblasts appeared to arrange themselves toward the center of the aggregates while HUVECs localized on the periphery surrounding the fibroblasts.

Example 4

Aggregation of Murine Mesothelial Cells and Macrophages

Murine malignant mesothelioma cells (40 L) were seeded alone and simultaneously in co-culture with normal primary peritoneal macrophages (MO) isolated from an eGFP-transgenic mouse, the latter of which were also seeded alone. In order to visualize the cells, cells suspended in CDMEM culture medium were stained with the blue fluorescent dye 4,6-diamino-2-phenylindole (DAPI—Vector Laboratories) in accordance with the manufacturer's protocol.

After staining, the three types of cell suspensions (homogeneous populations of mesothelioma and macrophage cells, and the mixed population of mesothelioma/macrophage cells) were seeded into the seeding chambers of aggregation devices made in accordance with Example 1 above. A total of 200 cells per aggregation recess were used; the mixed population in a 3:1 ratio of macrophage:mesothelioma cells. The three populations of cells were incubated for 2 days and then visualized using fluorescent microscopy. The homogeneous populations of mesothelioma cells formed spheroid aggregates within the aggregation recesses. The homogeneous populations of macrophages formed very loose aggregates within the aggregation recesses; they were not expected to form tight aggregates because they do not form intercellular junctions (in contrast to mesothelial or epithelial cells that attach to each other). However, while there was some variability among seeding chambers, in co-cultures, the macrophages formed aggregates with the neoplastic mesothelial cells in the aggregation recesses, similar to tumors in vivo.

Example 5

Encapsulation of Aggregated Fibroblast Cells

Aggregates of normal human diploid fibroblasts were made in accord with Examples 1 and 2 above. The cell aggregation devices were typically made the day before they would be used and were soaked in media for approximately 24 hours to equilibrate them prior to using.

Briefly, aggregation wells of 400 and 600 µm diameter were printed onto a wax mold using a three dimensional wax printer, and the gel was cast onto this wax mold, creating a negative of the original mold as illustrated in FIG. 1. Each well was cylindrical is shape and terminated in a hemisphere at one end. Cells were grown using conventional tissue culture technique. Once cells were grown to confluence, they were passed and resuspended to a cell density of $0.5 \times 10^6$ cells per gel or per device. Cells were seeded into the cell aggregation device by slowly adding 150 µl (about 500,000 cells) to each of the aggregation devices dropwise as illustrated in FIG. 2. The cells were allowed to sit and aggregates were typically observed 24 hours post-seeding. After aggregation, media was changed every other day for up to five days when aggregates were stable and mature. After five days, the cell aggregates were encapsulated in situ in the cell aggregation device as square sheets as described in Example 6.

Example 6

Preparation of Microarrays of Aggregates for Encapsulation

Reference to FIG. 5 may be made as the procedure detailed below is illustrated therein. Because even cell culture alginate has inherent impurities, a 1.8% sodium alginate (Sigma) in 1×Phosphate Buffered Saline (PBS) solution first was mixed in a sterile field, then centrifuged at 4000 rpm for 45 minutes to remove impurities. The supernatant was then filtered through a 0.42 µm syringe filter to obtain sterile alginate solution. The cell aggregation device from Example 5 was placed in an empty container, excess media bathing the aggregated cells was aspirated out as shown in step 1 of FIG. 5, and 300 µl of alginate, the maximum volume the upper cell suspension chamber in the cell aggregation device can hold, was slowly pipetted into the chamber as shown in step 2. Next, in step 3, a 0.15M solution of $CaCl_2$, was added and crosslinking was allowed to occur for up to one hour in the incubator. Because of the relatively low concentration of $CaCl_2$, the aggregates of cells do not die during the crosslinking period.

In step 4, once the gels were crosslinked, leftover $CaCl_2$ was aspirated out and the gels were allowed to dry at room temperature for between 2.5 to 3 hours. Because of the different dehydration rates of the alginate and the slower acrylamide, the alginate containing the aggregated cells was readily removed from the aggregation device. The alginate was peeled off the acrylamide aggregation device in the form of a sheet 17.6 by 17.6 mm with one aggregate per raised dome on one side of the microarray.

The alginate sheets were then visualized under an inverted light microscope and a microarray of encapsulated aggregates of cells was seen (FIG. 6). MTT (3-(4,5-dimethylthiazol-2-yl)-2,5-diphenyltetrazolium bromide) staining confirmed that all cells were alive and non-apoptotic. Because MTT staining may mask a necrotic core in aggregates, a live/dead stain (Molecular Probes) can be employed to discern the nature of the aggregate core. The live/dead stain consists of two stains, calcein-AM and ethidium homodimer (Eth-D). Calcein-AM is taken up by live cells where cytoplasmic esterases cleave it and allow it to fluoresce green. Dead cells do not take up calcein-AM, but instead, Eth-D is able to enter the dead cell's nucleus, staining it red. Live/ dead staining shows whether the core cells in the aggregate are viable. For storage, sheets were immersed in 3 mL culture media (Dulbecco's Modified Eagle Media (DMEM, Invitrogen), 10% Fetal Bovine Serum (FBS, Invitrogen) and 1% Penicillin-Streptomycin (Penn-Strep, Invitrogen)), and media was changed every other day.

Example 7

Application of Coating Layer to Encapsulated Live Cell Aggregates

The microarray of aggregated live fibroblast cells from Example 6 was then coated with a layer of poly-L-lysine to ensure complete encapsulation and to assist in stabilizing the alginate. A 5% stock solution of poly-L-lysine (MW=23, 400, Sigma) in sterile water was mixed and then filtered through a 0.42 μm syringe filter and then diluted to 0.1% by the addition of sterile water. The microarray was washed with water two to three times to eliminate salts from the storage media, the 0.1% PLL solution was then added and the microarray was placed in an incubator and allowed to crosslink for fifteen to twenty minutes, as illustrated in step 5 of FIG. 5. Afterwards, the PLL-water solution was aspirated out, and the microarray was washed once again with sterile water to eliminate excess PLL.

The general process as described in Examples 6 and 7 is illustrated in FIG. 5. In step 1, media was aspirated out of the cell suspension seeding chamber of the aggregation device. In step 2, 300 μl of alginate was gently pipetted into the chamber and onto the aggregated cells in their aggregation recesses. Next, in step 3 the $CaCl_2$ solution was pipetted into the device and crosslinking was allowed to occur. In step 4, excess $CaCl_2$ was aspirated out, the crosslinked alginate gel was allowed to air dry and then peeled off the acrylamide aggregation device. In the next step, the sheet of encapsulated cells were bathed in a solution of poly-L-lysine for an additional coating.

Example 8

Visualization Studies

To ensure the encapsulation layer and the coating layer completely encapsulate the cell aggregates, the alginate substrate and the PLL can be dyed and visualized under confocal microscopy. Fluoresceinamine ($C_{20}H_{13}NO_3$, Sigma) mixed in a concentration of 4.5 mM is incubated with 1.8% alginate solution, and stirred at room temperature. To removed unreacted dye, the solution can be dialyzed against ion-free water at 4° C. (26). PLL can be labeled by protein coupling to fluorochromes such as Alexa 546. By making the microarrays out of a solution of Fluoresceinamine-Alginate and coating with Alexa 546-PLL, the microarrays could be visualized using confocal microscopy, the results of which indicated that the PLL coating was uniform and regular.

For characterization studies, a similar protocol was followed using a 0.1% solution of FITC-PLL instead of PLL (MW=23,400, Sigma), and the microarrays made were kept wrapped in foil to prevent photobleaching of labeled PLL. By staining the outer coating, epi-fluoresence microscopy can confirm the location of cells relative to the outermost coating of the microarray. Cells can also be stained (Cell-Tracker, Molecular Probes) in order to co-localize aggregates with respect to PLL.

To avoid subjecting the microarrays to the mechanical stress required for SEM visualization, the samples can be visualized through an environmental scanning electron microscope (ESEM) to confirm complete encapsulation of the aggregates.

Example 9

Stable, Self-assembled, Non-spheroidal Aggregates of Cells

Using differently shaped aggregation devices of the invention, we have determined that different cells have different aggregation abilities and characteristics, and different structures and forms into which they will aggregate. For example, normal human fibroblasts (NHF) and rat hepatocytes cells (H35 cells) exhibit significant differences when they aggregate; in trough-shaped recesses, H35 cells readily form stable rod structures while NHF cells form spheroids. Both form tori, but H35 tori are more stable than NHF tori. These differences can be employed advantageously to construct stable, non-spheroidal structures of aggregated cells for tissue engineering applications, for example, replacing tissue engineering techniques such as microinjection of contiguous spheroids within a biocompatible matrix or electropatterning cells into desired arrays.

A. Some Form Rods, Some Form Spheres

Micro-molded, non-adhesive, cell aggregation devices, each having a plurality of cell aggregation recesses in the shape of either troughs or tori were made following the method described in Example 1. Agarose was employed as the hydrogel material and the cell aggregation recess features were as follows. Troughs were 400 μm wide with bottoms rounded with 200 μm radii. There were 21 rows of troughs of increasing length per gel. Each row had 11 troughs, two of which were 400 μm long, then one each of 600 μm through 1800 μm increasing at 200 μm lengths, then two 2200 μm troughs. The 2200 μm troughs were used for all experiments except those for FIG. 9c, which presents data from all trough lengths. Tori-shaped recesses were 800 μm deep, with circular track 400 μm wide. The recess bottom was filleted with radius 200 μm. The peg diameter was 600 μm and that of the entire feature was 1400 μm. There were 104 staggered tori per gel each separated by 250 μm.

NHF cells alone, H35 cells alone, and 50:50 mixtures of NHF and H35 cells were seeded into the trough aggregation devices and the tori aggregation devices as described in Example 2 and allowed to aggregate. Briefly, NHF cells derived from neonatal foreskins and H35 rat hepatoma cells were expanded in DMEM supplemented with 10% fetal bovine serum (FBS) and 1% penicillin/streptomycin solution. NHF cells were incubated in a 10% $CO_2$ atmosphere and H35 cells were incubated in 5% $CO_2$. The mixture experiments were a 50:50 mix of both cell types and were maintained in a 5% $CO_2$ atmosphere. The cells were stained with fluorescent dyes (NHF cells with CellTracker Red CMTPX and H35 cells with CellTracker Green CMFDA from Invitrogen) to allow their aggregation in the mixed populations to be followed and their aggregated position visualized. Cells used in experiments were between passage 3 and passage 9. Cell viability was determined using the LIVE/DEAD Viability/Cytotoxicity Kit (Invitrogen) in accordance with the manufacturer's instructions.

Excess medium was aspirated from the wells and 200 μL of a single cell suspension was pipetted into the aggregation recess of each gel. Medium was added to the wells after a 1.5 hour incubation period wherein cells settled into the aggregation recesses and commenced the self-assembly process. Medium was exchanged every other day. The aggregation process was observed with time-lapse microscopy using a Nikon TE2000-S microscope and a Hamamatsu Orca-ER camera, outputting to Openlab v4.0.2 (Improvision). A z-stack of images from the 4× objective with 10-50 μm between focal planes was collected at each time point using custom-designed Openlab 4.0.2 automations and images were analyzed using Volocity 3.1 (Improvision). Bright-field and fluorescent images were obtained using an Olympus IX70 microscope equipped with an AxioCam MRc digital camera. For the timelapse experiments, medium was carefully added 20-30 minutes post seeding, before the devices were transferred to the time lapse microscope. Measurements of morphological changes were performed with ImageJ data analysis software. The length of a rod was the length of a line drawn from end to end of the structure (long-axis length). The core circumference of tori was measured as a continuous circumferential line located at the estimated midpoint of the perpendicular width of the toroid.

Minutes post-seeding, cells settled into and coated the curved recess bottoms with several layers of cells but did not fill the recesses. Self-assembly began immediately with cells coalescing and compacting to form smooth surfaced 3D structures. In trough-shaped recesses, cells self-assembled into round-ended, cylindrical rods and shrank along their long-axes towards a spheroid morphology. NHF cells and mixture cells aggregated first into rods and then become spheroids in as few as 15 hours, but H35 cells maintained the rod morphology and did not form spheroids. The NHF cells, the H35 cells and the mixed cells all formed stable tori that conformed around the central peg of the torus substrate. Despite identical seeding densities and similar mean cell diameters (H35=17±2 μM, n=100; NHF=20±3 μM, n=20), there were clear morphological differences in the tori. The NHF toroid was thinnest while that of H35s was thickest. The thickness of the mixed cell population was less regular with foci of higher cell density connected by thinner regions. While both NHF and mixed cells could be aggregated into stable tori with an initial seeding density of $2 \times 10^6$ cells/gel, H35 cells could be aggregated into stable tori even with a seeding density as low as $1 \times 10^6$/gel (data not shown). Once aggregated into a rod or tori shape, the cells could be easily removed from the substrate. The removed aggregates maintained the final shape they had been formed into during aggregation in their respective trough and toroidal substrates.

To examine the kinetics of toroid and of rod formation, stability and morphological changes over time were measured. NHF cells, H35 cells and their 1:1 mix were seeded onto micro-molded gels with toroid or trough features. The number of stable toroids with patent centers was measured over time, n=728 (H35), 511 (NHF), 474 (Mixed). At day 5, there were significantly more intact H35 (88%) than NHF (30%) or mixed (60%) tori. Notably, stability of mixed tori was intermediate between that of H35 and NHF. Core circumferences of tori were maximal at time 0 when the cells coated the bottom of the recesses. As self-assembly proceeded, the core circumference decreased until the tori conformed to the peg. This process occurred at strikingly different rates between H35 cells and both NHF cells and mixtures. Steady state was achieved by day 2 in H35 cells, but in less than a day for both NHF cells and mixtures. These data show that stable tori have different core circumferences depending on cell type with NHF cells the shortest, H35 cells the longest and mixtures near midway between the two.

It is interesting to note that the rate of change in core circumference for mixtures and NHF cells were similar, but mixtures formed more stable tori than NHF cells. Only H35 cells differed in their kinetics of rod and toroid changes with core circumferences progressing at a slower rate than rod lengths (data not shown).

In trough-shaped recesses, the length of the aggregated H35 rods changed at a significantly slower rate than those of the aggregated NHF rods and the aggregated mixed rods. NHF and mixed rods become spheroids overnight, whereas H35 rods reached a final stability of 41% of their original length by day 5. Data on rods formed in troughs of increasing length suggest that this percentage remains constant, regardless of maximal length. Interestingly, while tori and troughs seeded with NHF cells and mixed cells progressed to their final aggregated morphology overnight, tori seeded H35 cells reached their final toroidal-shaped aggregated morphology in two days and troughs seeded with H35 cells needed 5 days to reach their final rod-shaped aggregated morphology. Mixed aggregates self-assembled with kinetics similar to aggregated NHF cells alone.

Time-lapse microscopy was used to investigate the early kinetics of rod and toroid self-assembly. Photos of rods in 1.6 mm troughs were taken at 10-minute intervals and long axis lengths were measured and plotted as a 20 function of time. When NHF rods began to self-assemble into aggregates, a necking or pinching in the middle and across the short axis was often observed. The initial length of NHF rods remained nearly static for 20-30 minutes before rapidly shrinking by 40% over 50 minutes followed by a transition to a slower period of further compaction (15%) over 1120 minutes. Necking began within 10-20 minutes, but rapidly reduced by 50% over 30 minutes only to increase over 1150 minutes to a value greater than its starting condition. Final length and width were nearly identical, indicating spheroid formation. Mixed rods also progressed to spheroids with kinetics similar to NHF cells (mixture tau=347 mins; NHF tau=202 mins). In contrast, there was no lag period for H35 rods and self-assembly proceeded with linear kinetics at a much slower rate (tau=$1.21 \times 10^8$ mins).

To evaluate cell sorting within mixture tori, the H35 cells and the NHF cells were differently labeled with fluorescent dyes as described above and allowed to self-assemble for two days. Sorting occurred within 24 hours in parallel with changes in core circumference and final cell type positions did not change between day 1 and day 2. NHF cells formed a central ring adjacent the toroid substrate; the H35 cells formed around and adjacent to the NHF cells in the aggregated structure. While some mixing was apparent, the NHF cells were clearly biased inwards towards the central peg, particularly in thicker regions of the toroid. NHF cell morphologies were stretched and more spindle-like, with less-distinct boundaries, most notably in areas of high stress. In contrast, H35 cells were more individual, rounded and spherical regardless of their position within the toroid. While more evenly distributed through the tori, they occupied the outermost regions away from the central peg. After 2 days, these positions were consistent and slightly more apparent than after the first day. By day 2, some of the mixed aggregates had moved up and off the central pegs altogether, and patent centers were still apparent.

In summary, in troughs up to 2.2 mm in length, H35 cells self-assembled into aggregated rod-like structures and did not form spheroids as would be predicted by many previous studies. NHF cells and the mixed populations did aggregate into spheroids. The kinetics of self-assembly revealed interesting differences as well. After a slight delay, NHF rod lengths decreased rapidly with exponential kinetics and then decreased more slowly while approaching spheroid morphology by 1100 minutes. In contrast, aggregated H35 rod lengths decreased with almost linear kinetics during the first 24 hours then with slower kinetics over the proceeding four days. Interestingly, the kinetics of the 1:1 mix of NHF cells and H35 cells was not intermediate but was more similar to the kinetics of aggregated NHF cells rather than aggregated H35 cells. The mix had the same slight delay followed by an exponential decrease in rod length with a curve that was nearly identical to that of aggregated NHF cells, except delayed by approximately 2 hours.

B. Directed, Self-Assembly and the Formation of Honeycomb Cell Aggregates

In this experiment, cell aggregation devices were formed from agarose gels as described above, but agarose gels were micromolded with honeycomb-shaped recesses instead of troughs or a tori. The honeycomb-shaped recesses are essentially overlapping, tori-shaped recesses: There are 13 pegs (1 central, 6 concentric around the central peg and 6 outer pegs at 0°, 60°, 120°, 180°, 240°, 300° and 360°) within a network of recesses 400 μM wide and with bottoms rounded with 200 μm radii. Time lapse microscopy was again used to monitor self-assembly of the NHF cells alone, the H35 cells alone and 50:50 mixtures of NHF cells and H35 cells as described above. The results are shown in FIG. 8, at time 0 (top row), 10 hours post-seeding (middle row) and 20 hours post-seeding (bottom row) with the aggregated NHF cells in column A, the aggregated H35 cells in column B and the aggregated 1:1 mixture of NHF and H35 cells in column C. The aggregated NHF cells quickly thinned, became taught and popped off the outer pegs of the honeycomb shaped substrate. Once freed from the substrate, the honeycomb-shaped aggregates of NHF cells contracted in a uniform. manner but maintained its shape. The aggregated H35 cells thinned more slowly, maintaining contact with the outer pegs and staying within the molds. The mixed cells exhibited an aggregation behavior intermediate between the aggregated NHF cells alone and the aggregated H35 cells alone. They thinned more quickly than the aggregated H35 cells alone and only partially popped off the pegs after 20 hours. Like the NHF aggregates, the architectural integrity of the resulting free-floating aggregated NHF/H35 mixed honeycombs was preserved as the cells aggregated and the structures contracted. Patency of the lumens was lost during this contraction process but the general shape of the structures did not progress to spheroids.

To assay self-segregation in this complex, branching structure, labeled H35 cells and NHF cells were seeded in the honeycomb mold and were viewed one and two days later. As in labeled tori, sorting occurred within 24 hours, with NHF cells centrally located toward the pegs and H35 cells on the periphery coating the entire structure. NHF cells had a spindle-like, stretched and smooth cell morphology (which relaxed to a rounder morphology when freed from the substrate), while H35 cells were more rounded with visible cell boundaries. Self-segregation varied with position in the honeycomb. Along the outer edge of the 6 most outer pegs, the fibroblasts were located less central and closer to the peg, as was the case for tori.

We also evaluated cell position and morphology of the mixture honeycomb-shaped aggregates that freed themselves from the pegs. In these relaxed structures, the patency of the lumens was maintained and the relative cell positions remained unchanged, but there was a significant change in fibroblast morphology. Instead of indistinct cell boundaries and elongated spindle-like morphologies found in taught structures, NHF cells in relaxed honeycombs were rounded and cell boundaries were easily discernible. This was in contrast to H35 cells that remained round and distinct from neighbors in both stretched and relaxed conformations.

The self-assembled honeycomb structures composed of the aggregated cells that were created in this experiment demonstrate that tension can be balanced and distributed throughout a complex self-assembled cellular structure without the need for a scaffold. Honeycombs of NHF cells, H35 cells and mixtures of NHF and H35 cells were each anchored by contact with the outer edge of the 6 outer pegs. The structure had little if any contact with the inner 7 pegs. The time-lapse experiments clearly show that the entire honeycomb structure is under tension and that the presence of NHF cells significantly increases this tension. Honeycombs of NHF cells and honeycombs of the NHF/H35 cell mixture spontaneously popped off the outer pegs and the structures quickly contracted.

As freed honeycomb aggregated cells shrank, their lumens narrowed. Shrinkage and narrowing was greatest for honeycombs of pure NHF cells, least for pure H35 cells and the NHF/H35 cell mixture was intermediate. Patency of the lumens was maintained for 2 days for NHF cells and as long as 5 days for H35 cells. Changes to the geometry of the mold such as increasing the diameter of the agarose pegs may help to increase patency as well as control lumen size. Maintenance of lumen patency is another significant difference between cell types in their self-assembly properties.

Tension also probably plays a role in the self-segregation of NHF cells and H35 cells in complex shapes. In spheroids, different cell types self-segregate and envelop one another due to differences in surface adhesion. Foty, et al., *Development* 122: 1611-20 (1996). This was observed for NHF cells and H35 cells in tori and honeycombs with NHF cells centrally located and H35 cells coating the periphery. However, in tori, the ring of NHF cells was not at the midpoint, but was located closer to the agarose peg. In honeycombs, the band of NHF cells on the outer edges of the outer pegs, an area of concentrated tension, was also closer to the agarose peg, but the band of NHF cells in the interior of the honeycomb, where tension was balanced, were more equally spaced.

That rod-shaped aggregates, tori-shaped aggregates and honeycomb-shaped aggregates could be generated with H35 cells, a parenchymal cell type, rather than NHF cells, a stromal cell type, is encouraging for microscale tissue engineering. Indeed, while we investigated a 1:1 ratio of H35 cells to NHF cells, the physiologic ratio of hepatocytes to fibroblasts is closer to 0.5:1. Bhatia et al., *Biotechnology progress* 14: 378-87 (1998). Together with our findings that mixtures had intermediate stabilities, this suggests that the constructs with more in vivo-like ratios and histologies may be more stable, and thus better to employ in tissue engineering applications.

In sum, self-assembled rod-like aggregations of cells and honeycomb aggregations of cells offer interesting new possibilities for the engineering of three-dimensional microtissues for in vitro and in vivo applications. Unlike a spheroid whose ultimate size is severely limited by diffusion, the length of a rod structure has no theoretical limit provided its radius remains within the critical diffusion limit needed to maintain cell viability. Enmon et al., *Biotechnology and bioengineering* 72, 579-591 (2001); Griffin et al., *Tissue Eng* 11: 257-66 (2005); Ambrosi et al., *Journal of Mathematical Biology* 48: 477-99 (2004). Such rod-like structures may have applications in bioreactors. The honeycomb, which is essentially a combination of rods and tori in a structural design, is well known as an efficient geometrical shape and may also have applications in bioreactors as well as in tissue engineering. Three dimensional branching micro tissues with open lumens more closely approximates the in vivo environment and lumen structures offer the possibility of enothelializing self-assembled micro tissues for transplantation.

Example 10

Drug Assisted Aggregation of Complex Microtissue Structures

The foregoing example demonstrated that the final aggregation structure normally attained by the aggregated cells are cell-type dependent and "pre-programmed", but that the pre-programmed structure may be modified by changing the shape of the aggregation device employed to aggregate the cells. This example goes further and demonstrates that the dynamics of cellular self-aggregation can be controlled by the administration of selected aggregation modifying agents during the aggregation process. In other words, the rate and extent of aggregation is controllable by the addition of selected aggregation modifying agents to the cells before aggregation begins. The experiment detailed below illustrates this principle using the known cell contraction inhibitor Y-27632, although any other agent that has the effect of modifying the dynamics of aggregation may be employed.

Micro-molded agarose toroidal aggregation devices (n=208) made as described in Example 9 were seeded with untreated NHFs and NHFs treated with 100 μM of the cell contraction inhibitor Y-27632 (Calbiochem (EMD Biosciences, Inc.), San Diego, Calif.) and the number of stable toroids with patent centers was measured over time. By day 1, all untreated NHFs (n=104) had progressed from toroids to spheroids while 90% of the treated NHFs (n=104) still had patent centers. By day 2, only 5% of the treated NHFs still had patent centers. This demonstrates that the native kinetics of cell aggregation can be modified by treatment of the cells with an aggregation inhibitor. The data is shown in the FIG. 9 histogram.

The effect was not limited to spheroidal cell aggregation structures. Next, aggregation devices with trough features 2.2 mm in length were made as described in previous examples and seeded with NHF cells, NHF cells in serum-free medium, NHF cells treated with 50 μM of Y-27632 and NHF cells treated with 200 μM of Y-27632 and the lengths of resulting rod shaped aggregates were measured. The results are shown in FIG. 10, in which NHFs are represented by the solid triangles (▲), NHFs in serum-free medium are represented by the clear triangles (Δ), NHFs treated with 50 μM of Y-27632 are represented by the inverted solid triangles (▼) and NHFs treated with 200 μM of Y-27632 are represented by the inverted clear triangles (∇). Increasing Y-27632 dramatically slowed length change kinetics in rods. H35 rods, which remain at 41% their trough length after 5 days, are included for reference are represented by the solid circles (●).

Gels with trough features 2.2 mm in length were then seeded with NHFs or with NHFs treated initially with 100 μM Y-27632 and imaged every 10 minutes. At 1.5 hrs, the Y-27632 solution was removed and replaced with normal medium. The results are shown in FIG. 11 in which the untreated NHFs are represented by the solid inverted triangle, the treated NHFs are represented by the clear inverted triangle and the arrow indicates the change of media at 1.5 hrs. The results demonstrate that upon removal of the aggregation inhibiting drug, the NHF cells aggregated into rods, progressing with similar kinetics to those of untreated NHFs.

Lastly, NHFs were seeded onto honeycomb-structured cell aggregation devices made as described in Example 9B and maintained in Y-27632 solution. While untreated NHFs contracted up and off of pegs within 1 day, treated NHFs remained intact in the honeycomb-shaped recesses at day 5. An example of one treated NHF honeycomb is shown in FIG. 12. Viability staining revealed that the majority of the cells were living at day 5.

These results demonstrate that the native kinetics of cell aggregation in the cell aggregation devices of the invention may be modified by treatment of the cells with an aggregation inhibitor. Accordingly, the kinetics of aggregation can be controlled by treatment with aggregation modifying agents to either speed up or slow down aggregation as needed by the treatment regimen and the tissue repair and/or reconstruction protocol.

All of the compositions and methods disclosed and claim herein can be made and executed without undue experimentation in light of the disclosure. Although the compositions and methods of the invention have been described in terms of preferred embodiments, it will be apparent to those having ordinary skill in the art that variations may be made to the compositions and methods without departing from the concept, spirit and scope of the invention. Fore example, certain agents and compositions that are chemically related may be substituted for the agents described herein if the same or similar results would be achieved. All such similar substitutes and modifications apparent to those skilled in the art are deemed to be within the spirit, scope and concept of the invention.

All publications, patent applications, patents and other documents cited herein are incorporated by reference in their entirety. In case of conflict, this specification including definitions will controL In addition the material methods and examples are illustrative only and not intended to be limiting.

What is claimed is:
1. A method of aggregating cells, comprising the steps of:
 a) depositing a plurality of cells into an upper cell suspension seeding chamber of a cell aggregation device having a biocompatible, polymeric hydrogel substrate that includes an upper surface and a lower surface and having at least one compartment at least partially recessed into the upper surface, the compartment being composed of the upper cell suspension seeding chamber, at least one lower cell aggregation recess and a port extending there between, the upper cell suspension seeding chamber being formed and positioned to funnel cells into the lower cell aggregation recess via the port through gravitational force and the lower cell aggregation recess being composed of a cell-repellant hydrogel and being formed and positioned to coalesce the cells into a finite region of minimum gravitational energy; and
 b) incubating the cells for time sufficient to allow the cells to be funneled from the upper cell seeding chamber to the lower cell aggregation recess by gravity through the port and into the finite region; and
 c) incubating the cells for a time sufficient to allow the cells to aggregate in the finite region of the lower cell aggregation recess.
2. The method of claim 1, further comprising the step of adding a selected aggregation modifying agent to the cells during the time sufficient to allow the cells to aggregate in the finite region of the lower cell aggregation recess.

3. The method of claim 1, wherein said cells are selected from the group consisting of osteoblasts, keratinocytes, melanocytes, hepatocytes, gliacytes, pancreatic beta cells, pancreatic exocrine cells, neural stem cells, neural precursor cells, spinal cord precursor cells, nerve cells, mammary gland cells, salivary gland cells, renal glomerular endothelial cells, tubular epithelial cells, adrenocortical and adrenomedullary cells, cardiomyocytes, chondrocytes, skeletal and smooth muscle cells, fat and fat precursor cells, corneal and crystalline lens cells, embryonic retina cells, vascular cells, endothelial cells, bone marrow stromal cells, lymphocytes, smooth muscle cells, skeletal muscle cells, cardiac muscle cells, connective tissue cells, epithelial cells, nervous system cells and nonhuman embryonic stem cells, non-embryonic and hematopoietic mammalian stem cells.

4. The method of claim 3, wherein the connective tissue cells are at least one member selected from the group consisting of a fibroblast, a monocyte, a mast cell, a granulocyte, a plasma cell, an osteoclast, an osteocyte and a chondrocyte.

5. The method of claim 3, wherein the epithelial cells at least one member selected from the group consisting of a skin epithelial cell, a gastrointestinal epithelial cell, a urinary tract epithelial cell, a reproductive tract epithelial cell, a liver epithelial cell, a pancreas epithelial cell, and a spleen epithelial cell.

6. The method of claim 3, wherein the nervous system cell is at least one member selected from the group consisting of a glial cell, a neuronal cell and an astrocytes.

7. The method of claim 1, further including the step of removing the aggregated cells from the lower aggregation recess.

* * * * *